(12) United States Patent
Mindell et al.

(10) Patent No.: US 12,080,415 B2
(45) Date of Patent: Sep. 3, 2024

(54) RADIO-FREQUENCY SYSTEMS AND METHODS FOR CO-LOCALIZATION OF MEDICAL DEVICES AND PATIENTS

(71) Applicant: Humatics Corporation, Waltham, MA (US)

(72) Inventors: David A. Mindell, Cambridge, MA (US); James Campbell Kinsey, Brookline, MA (US); Gregory L. Charvat, Guilford, CT (US); Matthew Carey, Hooksett, NH (US); Devon Reed Clark, Boston, MA (US); Eben Christopher Rauhut, Watertown, MA (US); Jyotsna Marie Winsor, Somerville, MA (US)

(73) Assignee: Humatics Corporation, Waltham, MA (US)

( * ) Notice: Subject to any disclaimer, the term of this patent is extended or adjusted under 35 U.S.C. 154(b) by 467 days.

(21) Appl. No.: 17/497,551

(22) Filed: Oct. 8, 2021

(65) Prior Publication Data
US 2022/0115123 A1  Apr. 14, 2022

Related U.S. Application Data

(60) Provisional application No. 63/089,942, filed on Oct. 9, 2020.

(51) Int. Cl.
*H04B 5/77* (2024.01)
*G06K 7/10* (2006.01)
(Continued)

(52) U.S. Cl.
CPC ......... *G16H 40/63* (2018.01); *G06K 7/10366* (2013.01); *G06K 19/0723* (2013.01); *G16H 30/20* (2018.01); *H04B 5/77* (2024.01)

(58) Field of Classification Search
CPC ........ G16H 40/63; G16H 30/20; G16H 30/40; G16H 40/20; G16H 40/67; G06K 7/10366; G06K 19/0723; G06K 17/00; H04B 5/77
See application file for complete search history.

(56) References Cited

U.S. PATENT DOCUMENTS 2,851,681 A  9/1958  Cohn
3,631,484 A  12/1971  Augenblick
(Continued)

FOREIGN PATENT DOCUMENTS

CN  1094515 A  11/1994
CN  1839325 A  9/2006
(Continued)

OTHER PUBLICATIONS

International Search Report and Written Opinion for International Application No. PCT/US2021/042377 mailed Oct. 18, 2021.
(Continued)

*Primary Examiner* — Chad A Newton
(74) *Attorney, Agent, or Firm* — Wolf, Greenfield & Sacks, P.C.

(57) ABSTRACT

Systems and methods for facilitating interactions between a medical device (e.g., an imaging device, a surgical tool, a robotic arm, etc.) and a patient using radio frequency (RF) co-localization are provided. The systems include a radio-frequency (RF) interrogator system, one or more first RF target devices for coupling to a patient support for supporting a patient with respect to whom a medical device is to perform a task, and one or more second RF target devices for coupling to the medical device. A controller determines a position of the patient support within an RF interrogator system reference frame, a first position of the medical device within the RF interrogator system reference frame, a transformation between the RF interrogator system reference
(Continued)

frame and a patient support reference frame, and a second position of the medical device within the patient support reference frame.

20 Claims, 18 Drawing Sheets

(51) Int. Cl.
  *G06K 19/07* (2006.01)
  *G16H 30/20* (2018.01)
  *G16H 40/63* (2018.01)

(56) References Cited

U.S. PATENT DOCUMENTS

| | | |
|---|---|---|
| 3,706,096 A | 12/1972 | Hammack |
| 3,781,879 A | 12/1973 | Staras |
| 3,996,590 A | 12/1976 | Hammack |
| 4,001,822 A | 1/1977 | Sterzer |
| 4,217,549 A | 8/1980 | Henoch |
| 4,859,934 A | 8/1989 | Gale et al. |
| 5,045,856 A | 9/1991 | Paoletti |
| 5,108,027 A | 4/1992 | Warner et al. |
| 5,111,202 A | 5/1992 | Rivera et al. |
| 5,115,245 A | 5/1992 | Wen et al. |
| 5,355,283 A | 10/1994 | Marrs et al. |
| 5,402,442 A | 3/1995 | Ishigaki |
| 5,465,099 A | 11/1995 | Mitsui et al. |
| 5,495,255 A | 2/1996 | Komatsu et al. |
| 5,523,749 A | 6/1996 | Cole et al. |
| 5,832,369 A | 11/1998 | Bradley et al. |
| 5,898,907 A | 4/1999 | Maruyama |
| 6,046,683 A | 4/2000 | Pidwerbetsky |
| 6,084,530 A | 7/2000 | Pidwerbetsky et al. |
| 6,114,971 A | 9/2000 | Nysen |
| 6,150,921 A | 11/2000 | Werb et al. |
| 6,192,222 B1 | 2/2001 | Greeff et al. |
| 6,225,955 B1 | 5/2001 | Chang et al. |
| 6,259,408 B1 | 7/2001 | Brady et al. |
| 6,297,773 B1 | 10/2001 | Fullerton et al. |
| 6,353,406 B1 | 3/2002 | Lanzl et al. |
| 6,356,764 B1 | 3/2002 | Ovard et al. |
| 6,369,710 B1 | 4/2002 | Poticny et al. |
| 6,414,849 B1 | 7/2002 | Chiu |
| 6,480,143 B1 | 11/2002 | Kruger et al. |
| 6,600,443 B2 | 7/2003 | Landt |
| 6,633,226 B1 | 10/2003 | Nysen |
| 6,657,549 B1 | 12/2003 | Avery |
| 6,667,724 B2 | 12/2003 | Barnes et al. |
| 6,693,557 B2 | 2/2004 | Arnold et al. |
| 6,693,581 B2 | 2/2004 | Gottwald et al. |
| 6,762,681 B1 | 6/2004 | Danelski |
| 6,803,851 B1 | 10/2004 | Kramer et al. |
| 6,812,824 B1 | 11/2004 | Goldinger et al. |
| 6,868,073 B1 | 3/2005 | Carrender |
| 6,914,579 B2 | 7/2005 | Schadler |
| 6,958,677 B1 | 10/2005 | Carter |
| 7,023,321 B2 | 4/2006 | Brillon et al. |
| 7,088,964 B2 | 8/2006 | O |
| 7,145,453 B2 | 12/2006 | Miller, Jr. et al. |
| 7,193,504 B2 | 3/2007 | Carrender et al. |
| 7,253,717 B2 | 8/2007 | Armstrong et al. |
| 7,253,719 B2 | 8/2007 | Diorio et al. |
| 7,259,676 B2 | 8/2007 | Knadle, Jr. et al. |
| 7,323,994 B2 | 1/2008 | Yamagajo et al. |
| 7,385,551 B2 | 6/2008 | Stephens |
| 7,388,464 B2 | 6/2008 | Ward et al. |
| 7,479,884 B1 | 1/2009 | Fullerton et al. |
| 7,504,949 B1 | 3/2009 | Rouaix et al. |
| 7,504,992 B2 | 3/2009 | Pilcher, Jr. et al. |
| 7,526,266 B2 | 4/2009 | Al-Mahdawi |
| 7,567,206 B1 | 7/2009 | Schmidt et al. |
| 7,580,378 B2 | 8/2009 | Carrender et al. |
| 7,592,898 B1 | 9/2009 | Ovard et al. |
| 7,626,488 B2 | 12/2009 | Armstrong et al. |
| 7,649,491 B2 | 1/2010 | Ohara et al. |
| 7,800,507 B2 | 9/2010 | Light et al. |
| 7,801,491 B2 | 9/2010 | Hatakeyama et al. |
| 7,903,022 B2 | 3/2011 | Ohara et al. |
| 7,924,160 B1 | 4/2011 | Lapenta et al. |
| 7,965,191 B2 | 6/2011 | Rofougaran |
| 7,979,033 B2 | 7/2011 | Rofougaran |
| 8,060,400 B2 | 11/2011 | Wellman |
| 8,063,744 B2 | 11/2011 | Wu et al. |
| 8,073,562 B2 | 12/2011 | Danelski |
| 8,081,117 B2 | 12/2011 | Nagai et al. |
| 8,261,997 B2 | 9/2012 | Gebhart |
| 8,264,226 B1 | 9/2012 | Olsson et al. |
| 8,279,112 B2 | 10/2012 | Carrick |
| 8,351,968 B2 | 1/2013 | Ovard et al. |
| 8,446,254 B2 | 5/2013 | Carrick et al. |
| 8,525,648 B1 | 9/2013 | Henty |
| 8,576,075 B2 | 11/2013 | Reynolds |
| 8,643,536 B2 | 2/2014 | Cavirani et al. |
| 8,723,720 B2 | 5/2014 | Moffatt et al. |
| 8,730,014 B2 | 5/2014 | Fullerton |
| 8,855,169 B2 | 10/2014 | Ovard et al. |
| 9,041,514 B2 | 5/2015 | Nogami |
| 9,141,836 B2 | 9/2015 | Domokos et al. |
| 9,413,418 B2 | 8/2016 | Bottazzi et al. |
| 9,424,749 B1 | 8/2016 | Reed et al. |
| 9,485,037 B1 | 11/2016 | Weller et al. |
| 9,489,813 B1 | 11/2016 | Beigel |
| 9,514,342 B1 | 12/2016 | Hosseini et al. |
| 9,562,396 B2 | 2/2017 | Baym et al. |
| 9,608,313 B2 | 3/2017 | Kim et al. |
| 9,694,977 B2 | 7/2017 | Aprea et al. |
| 9,755,317 B2 | 9/2017 | Grelier et al. |
| 9,768,837 B2 | 9/2017 | Charvat et al. |
| 9,797,988 B2 | 10/2017 | Charvat et al. |
| 9,842,288 B1 | 12/2017 | DeBates et al. |
| 9,903,939 B2 | 2/2018 | Charvat et al. |
| 9,915,725 B1 | 3/2018 | Charvat et al. |
| 10,005,184 B2 | 6/2018 | Gerio et al. |
| 10,073,162 B2 | 9/2018 | Charvat et al. |
| 10,074,889 B2 | 9/2018 | Charvat et al. |
| 10,094,909 B2 | 10/2018 | Charvat et al. |
| 10,099,374 B2 | 10/2018 | Beosen |
| 10,121,122 B2 | 11/2018 | Russell et al. |
| 10,168,419 B2 | 1/2019 | Trummer |
| 10,205,218 B2 | 2/2019 | Charvat et al. |
| 10,422,870 B2 | 9/2019 | Mindell et al. |
| 10,505,256 B2 | 12/2019 | Charvat et al. |
| 10,591,592 B2 | 3/2020 | Mindell et al. |
| 10,665,923 B2 | 5/2020 | Charvat et al. |
| 10,695,099 B2 | 6/2020 | Scholl |
| 10,783,991 B1* | 9/2020 | LaBorde ............... G06Q 50/22 |
| 10,992,024 B2 | 4/2021 | Charvat et al. |
| 11,047,961 B2 | 6/2021 | Shimizu et al. |
| 11,050,133 B2 | 6/2021 | Charvat et al. |
| 11,050,134 B2 | 6/2021 | Charvat et al. |
| 11,050,497 B2 | 6/2021 | Charvat et al. |
| 2002/0070846 A1 | 6/2002 | Bastian, II et al. |
| 2002/0071435 A1 | 6/2002 | Bolgiano et al. |
| 2003/0020173 A1 | 1/2003 | Huff et al. |
| 2003/0161419 A1 | 8/2003 | Bach et al. |
| 2004/0008114 A1 | 1/2004 | Sawyer |
| 2004/0257267 A1 | 12/2004 | Mafune et al. |
| 2005/0012653 A1 | 1/2005 | Heide et al. |
| 2005/0075080 A1 | 4/2005 | Zhang |
| 2005/0156806 A1 | 7/2005 | Ohta et al. |
| 2005/0207481 A1 | 9/2005 | Forstner |
| 2005/0237953 A1 | 10/2005 | Carrender et al. |
| 2006/0250935 A1 | 11/2006 | Hamamoto et al. |
| 2006/0283252 A1 | 12/2006 | Liu et al. |
| 2007/0013599 A1 | 1/2007 | Gaucher et al. |
| 2007/0023020 A1 | 2/2007 | Miyashita |
| 2007/0055949 A1 | 3/2007 | Thomas |
| 2007/0106152 A1* | 5/2007 | Kantrowitz ............ A61B 90/39<br>340/572.1 |
| 2007/0164420 A1 | 7/2007 | Chen et al. |
| 2007/0182949 A1 | 8/2007 | Niclass |
| 2007/0206661 A1 | 9/2007 | Okada et al. |
| 2007/0237029 A1 | 10/2007 | Watson |

(56) References Cited

U.S. PATENT DOCUMENTS

| | | |
|---|---|---|
| 2008/0088503 A1 | 4/2008 | Beasley |
| 2008/0129487 A1 | 6/2008 | Crucs |
| 2008/0143584 A1 | 6/2008 | Shoarinejad et al. |
| 2008/0158081 A1 | 7/2008 | Rofougaran |
| 2008/0158084 A1 | 7/2008 | Rofougaran |
| 2008/0166978 A1 | 7/2008 | Cheah et al. |
| 2008/0198065 A1 | 8/2008 | Voigtlander et al. |
| 2008/0204238 A1 | 8/2008 | White |
| 2008/0205495 A1 | 8/2008 | Trott |
| 2008/0224874 A1 | 9/2008 | Rodgers |
| 2008/0231420 A1 | 9/2008 | Koyama et al. |
| 2008/0311862 A1 | 12/2008 | Spina et al. |
| 2009/0048865 A1 | 2/2009 | Breazeale, Jr. |
| 2009/0073054 A1 | 3/2009 | Yoon et al. |
| 2009/0079576 A1 * | 3/2009 | Yankelevitz ............ A61B 6/037 340/573.7 |
| 2009/0102716 A1 | 4/2009 | Sego |
| 2009/0154377 A1 | 6/2009 | Tsuda et al. |
| 2009/0201152 A1 | 8/2009 | Karr et al. |
| 2009/0201169 A1 | 8/2009 | d'Hont et al. |
| 2009/0267765 A1 * | 10/2009 | Greene ................ G06K 7/0008 340/568.1 |
| 2009/0315777 A1 | 12/2009 | Baughman |
| 2009/0322491 A1 | 12/2009 | Wood, Jr. |
| 2010/0039247 A1 | 2/2010 | Ziegler et al. |
| 2010/0063670 A1 | 3/2010 | Brzezinski et al. |
| 2010/0073188 A1 | 3/2010 | Mickle et al. |
| 2010/0102931 A1 | 4/2010 | Nikitin et al. |
| 2010/0109903 A1 | 5/2010 | Carrick |
| 2010/0117823 A1 | 5/2010 | Wholtjen |
| 2010/0167662 A1 | 7/2010 | Kluge et al. |
| 2010/0207820 A1 | 8/2010 | Kawano et al. |
| 2010/0297956 A1 | 11/2010 | Hayashi et al. |
| 2010/0302117 A1 | 12/2010 | Johnson |
| 2010/0328073 A1 | 12/2010 | Nikitin et al. |
| 2011/0007758 A1 | 1/2011 | Macrae |
| 2011/0109442 A1 | 5/2011 | Pavlov et al. |
| 2011/0140884 A1 | 6/2011 | Santiago et al. |
| 2011/0163882 A1 | 7/2011 | August et al. |
| 2011/0181892 A1 | 7/2011 | Ritter et al. |
| 2011/0181892 A1 | 8/2011 | Nikitin et al. |
| 2011/0279261 A1 | 11/2011 | Gauger et al. |
| 2011/0285606 A1 | 11/2011 | De Graauw et al. |
| 2012/0105300 A1 | 5/2012 | Ando et al. |
| 2012/0116665 A1 | 5/2012 | Aoki et al. |
| 2012/0146834 A1 | 6/2012 | Karr |
| 2012/0158235 A1 | 6/2012 | Jaynes |
| 2012/0182129 A1 | 7/2012 | Eggers et al. |
| 2012/0262329 A1 | 10/2012 | Molyneux et al. |
| 2013/0016023 A1 | 1/2013 | Gaucher et al. |
| 2013/0023210 A1 | 1/2013 | Roufougaran |
| 2013/0150160 A1 | 6/2013 | El Dokor et al. |
| 2013/0162491 A1 | 6/2013 | Yu |
| 2013/0307742 A1 | 11/2013 | Hu et al. |
| 2013/0321095 A1 | 12/2013 | Lam et al. |
| 2013/0342321 A1 | 12/2013 | Zogg et al. |
| 2014/0096871 A1 | 4/2014 | Kaye |
| 2014/0135042 A1 | 5/2014 | Buchheim et al. |
| 2014/0138109 A1 | 5/2014 | Duncan et al. |
| 2014/0214631 A1 | 7/2014 | Hansen |
| 2014/0253296 A1 | 9/2014 | Arthaber |
| 2014/0347222 A1 | 11/2014 | Ling |
| 2014/0349675 A1 | 11/2014 | Schatzberg et al. |
| 2014/0359540 A1 | 12/2014 | Kelsey et al. |
| 2015/0019391 A1 | 1/2015 | Kumar et al. |
| 2015/0048907 A1 | 2/2015 | Almgren et al. |
| 2015/0151913 A1 | 6/2015 | Wong et al. |
| 2015/0282115 A1 | 10/2015 | Pitt et al. |
| 2015/0379317 A1 | 12/2015 | Kelly et al. |
| 2015/0379791 A1 | 12/2015 | Russell et al. |
| 2016/0063429 A1 | 3/2016 | Varley et al. |
| 2016/0104109 A1 | 4/2016 | Singel et al. |
| 2016/0190696 A1 | 6/2016 | Preradovic et al. |
| 2016/0247006 A1 | 8/2016 | Hansen |
| 2016/0274586 A1 | 9/2016 | Stubbs et al. |
| 2016/0275391 A1 | 9/2016 | Sattlegger et al. |
| 2016/0301125 A1 | 10/2016 | Kim et al. |
| 2016/0311388 A1 | 10/2016 | Diewald |
| 2016/0358440 A1 | 12/2016 | Trivelpiece et al. |
| 2016/0363648 A1 | 12/2016 | Mindell et al. |
| 2016/0363659 A1 | 12/2016 | Mindell et al. |
| 2016/0363663 A1 | 12/2016 | Mindell et al. |
| 2016/0363664 A1 | 12/2016 | Mindell et al. |
| 2016/0370456 A1 | 12/2016 | Emanuelsson |
| 2017/0098888 A1 | 4/2017 | Geary et al. |
| 2017/0157783 A1 | 6/2017 | Ogawa |
| 2017/0158169 A1 | 6/2017 | Luo et al. |
| 2017/0176572 A1 | 6/2017 | Charvat et al. |
| 2017/0179570 A1 | 6/2017 | Charvat et al. |
| 2017/0179571 A1 | 6/2017 | Charvat et al. |
| 2017/0179602 A1 | 6/2017 | Charvat et al. |
| 2017/0179603 A1 | 6/2017 | Charvat et al. |
| 2017/0180011 A1 | 6/2017 | Charvat et al. |
| 2017/0181118 A1 * | 6/2017 | Charvat ............... H04W 4/023 |
| 2017/0201005 A1 | 7/2017 | Charvat et al. |
| 2017/0252112 A1 | 9/2017 | Crawford et al. |
| 2017/0328980 A1 | 11/2017 | Charvat et al. |
| 2017/0363709 A1 | 12/2017 | Charvat et al. |
| 2017/0371026 A1 | 12/2017 | Charvat et al. |
| 2018/0067190 A1 | 3/2018 | Charvat et al. |
| 2018/0115905 A1 | 4/2018 | Sirotkin |
| 2018/0156889 A1 | 6/2018 | Charvat et al. |
| 2018/0231651 A1 | 8/2018 | Charvat |
| 2018/0239010 A1 | 8/2018 | Mindell et al. |
| 2018/0375190 A1 | 12/2018 | Charvat et al. |
| 2019/0168712 A1 | 6/2019 | Yakovenko et al. |
| 2019/0173157 A1 | 6/2019 | Charvat et al. |
| 2019/0361109 A1 | 11/2019 | Mindell et al. |
| 2020/0052374 A1 | 2/2020 | Charvat et al. |
| 2020/0103492 A1 | 4/2020 | Zai et al. |
| 2020/0274226 A1 | 8/2020 | Charvat et al. |
| 2020/0341137 A1 | 10/2020 | Mindell et al. |
| 2020/0395118 A1 * | 12/2020 | Codd .................... G16H 40/40 |
| 2020/0405410 A1 * | 12/2020 | Shelton, IV ........... A61B 34/25 |

FOREIGN PATENT DOCUMENTS

| | | |
|---|---|---|
| CN | 101002236 A | 7/2007 |
| CN | 101166030 A | 4/2008 |
| CN | 101517905 A | 8/2009 |
| CN | 102667521 A | 9/2012 |
| CN | 102739265 A | 10/2012 |
| CN | 103064057 A | 4/2013 |
| CN | 103336936 A | 10/2013 |
| CN | 103959659 A | 7/2014 |
| CN | 104422927 A | 3/2015 |
| CN | 204539116 U | 8/2015 |
| EP | 1939980 A1 | 7/2008 |
| EP | 2829890 A1 | 1/2015 |
| GB | 2260065 A | 3/1993 |
| JP | H03-199988 A | 8/1991 |
| JP | H08-86855 A | 4/1996 |
| JP | 2001-223525 A | 8/2001 |
| JP | 2002-243849 A | 8/2002 |
| JP | 3570163 B2 | 9/2004 |
| JP | 2005-069892 A2 | 3/2005 |
| JP | 2007-533976 A | 11/2007 |
| JP | 2008-201569 A | 9/2008 |
| JP | 2014-516221 A | 7/2014 |
| JP | 2014-190980 A | 10/2014 |
| WO | WO 2005/103755 A1 | 11/2005 |
| WO | WO 2016/205216 A1 | 12/2016 |
| WO | WO 2016/205217 A1 | 12/2016 |
| WO | WO 2016/205218 A1 | 12/2016 |
| WO | WO 2016/205219 A1 | 12/2016 |
| WO | WO 2018/183571 A1 | 10/2018 |

OTHER PUBLICATIONS

International Search Report and Written Opinion for International Application No. PCT/US2016/037404 dated Sep. 16, 2016.
Invitation to Pay Additional Fees for International Application No. PCT/US2016/037406 dated Aug. 5, 2016.

(56) References Cited

OTHER PUBLICATIONS

International Search Report and Written Opinion for International Application No. PCT/US2016/037406 dated Oct. 26, 2016.
International Search Report and Written Opinion for International Application No. PCT/US2016/037403 dated Sep. 1, 2016.
International Search Report and Written Opinion for International Application No. PCT/US2016/037407 dated Sep. 2, 2016.
International Search Report and Written Opinion for International Application No. PCT/US16/67265 dated Apr. 14, 2017.
Extended European Search Report for European Application No. 16812242.2 dated Feb. 11, 2019.
Extended European Search Report for European Application No. 16876808.3 dated Aug. 5, 2019.
International Search Report and Written Opinion for International Application No. PCT/US2020/029522 mailed Jul. 16, 2020.
Communication pursuant to Article 94(3) EPC for European Application No. 16876808.3 dated Oct. 13, 2021.
[No Author Listed] Adafruit NeoPixel Digital RGB LED Strip—White 30 LED—White. 7 Pages. https://www.adafruit.com/products/1376 Last accessed Jan. 3, 2017.
Chalvatzis, An Injection-Locked 8.5 GHz VCO with Decade-Wide Programmable Locking Range in SiGe BiCMOS. IEEE. 2015;101-4.
Charvat et al., Harmonic Radar Tag Measurement and Characterization. IEEE. 2003;696-9.
Charvat et al., Time-of-Flight Microwave Camera. Sci. Rep. 5:14709; doi:10.1038/srep14709. 2015;1-6.
Charvat, Police Doppler Radar and Motion Sensors. In: Small and Short Range Radar Systems. 2014. Charvat, Chapter 8:20 pages.
Charvat, Continuous Wave (CW) Radar. In: Small and Short Range Radar Systems. 2014. Charvat, Chapter 2:34 pages.
Charvat, Frequency Modulated Continuous Wave (FMCW) Radar. In: Small and Short Range Radar Systems. 2014. Charvat, Chapter 3:71 pages.
Cho et al., A frequency agile floating-patch MEMS antenna for 42 GHz applications. 0-7803-883-6/05. IEEE. 2005;512-5.
Follmann et al., A Low-Noise 8-12 GHz Fractional-N PLL in SiGe BiCMOS Technology. Proceedings of the 5th European Microwave Integrated Circuits Conference. EuMA. 2010;98-101.
Ravinuthula et al., A Low Power High Performance PLL with Temperature Compensated VCO in 65nm CMOS. 2016 IEEE Radio Frequency Integrated Circuits Symposium. IEEE. 2016;31-34.
Saiz et al., A 135GHz SiGe Transmitter With A Dielectric Rod Antenna-In-Package For High EIRP/Channel Arrays. Proceedings of the IEEE 2014 Custom Integrated Circuits Conference, Sep. 15-17, 2014;1-4.
Tang et al., 183GHz 13.5mW/Pixel CMOS Regenerative Receiver for mm-Wave Imaging applications. ISSCC 2011/Session 16/mm-Wave Design Techniques/ 16.10. IEEE International Solid-State Circuits Conference. 2011;296-8.
Yan et al., A 8.3-11.3GHz low cost Integer-N synthesizer with 1.1° RMS phase error in 65nm CMOS. IEEE. 2012;225-7.
Yamashita et al., Variable polarization/frequency division multiplexing (VPFDM) for satellite communications. IEEE Vehicular Technology Conference Sep. 25, 2006:1-9.

\* cited by examiner

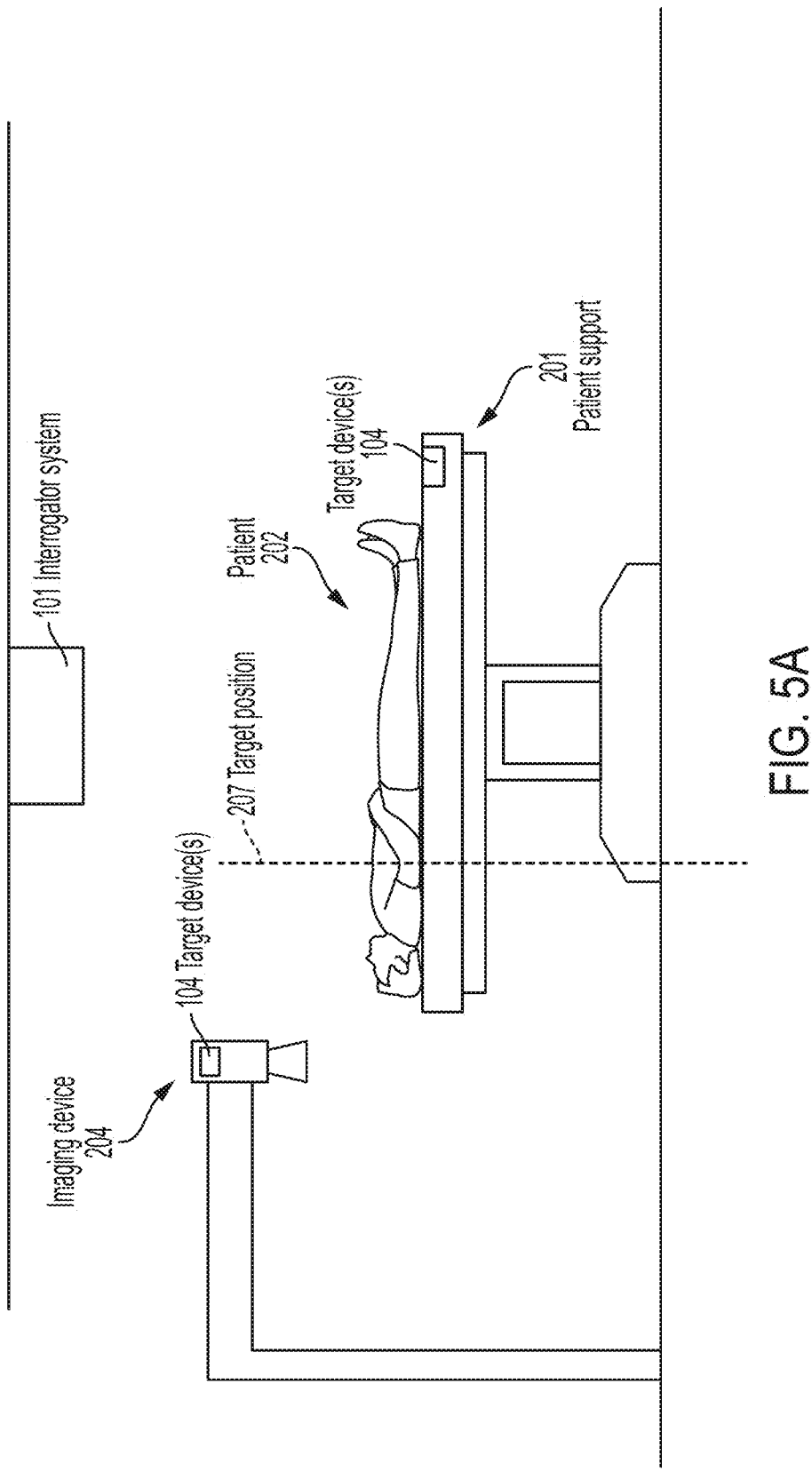

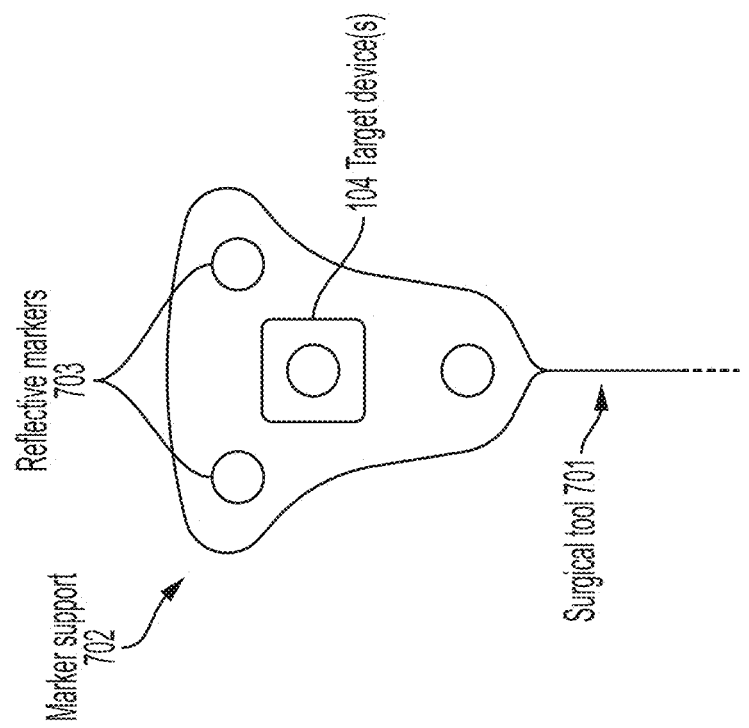

| Parameter | Value |
|---|---|
| Total update rate | 125 positions per second |
| Range | 6m maximum |
| Field-of-View | ± 40° |
| Position Precision : Boresight to ±5° | ± 1 mm |
| Position Accuracy : Boresight to ±5° | ± 1 cm |
| Position Precision: ±5° to 40° | ± 5 mm |
| Position Accuracy: ±5° to 40° | ± 4 cm |

FIG. 8A

RADIO-FREQUENCY SYSTEMS AND METHODS FOR CO-LOCALIZATION OF MEDICAL DEVICES AND PATIENTS

CROSS-REFERENCE TO RELATED APPLICATIONS

This application claims priority under 35 U.S.C. § 119(e) to U.S. Provisional Patent Application Ser. No. 63/089,942, titled "SYSTEMS AND METHODS FOR TRACKING ITEMS USING RADIO-FREQUENCY (RF) MICRO-LOCATION," filed on Oct. 9, 2020, which is incorporated by reference in its entirety herein.

BACKGROUND

Medical environments, such as emergency rooms, intensive care units, operating rooms, delivery rooms, etc., typically have a mix of personnel and medical equipment working side by side. Diagnostic medical imaging is a technique commonly used in medical environments.

SUMMARY

Some embodiments relate to a system comprising a radio-frequency (RF) interrogator system; one or more first RF target devices for coupling to a patient support for supporting a patient with respect to whom a medical device is to perform a task; one or more second RF target devices for coupling to the medical device; and a controller. The controller is configured to, when the one or more first RF target devices are coupled to the patient support and the one or more second RF target devices are coupled to the medical device, control the RF interrogator system to transmit one or more first RF signals; control the RF interrogator system to receive one or more second RF signals transmitted by the one or more first RF target devices responsive to the one or more first RF signals and one or more third RF signals transmitted by the one or more second RF target devices responsive to the one or more first RF signals; determine, using the received one or more second RF signals, a position of the patient support within an RF interrogator system reference frame; determine, using the received one or more third RF signals, a first position of the medical device within the RF interrogator system reference frame; determine a transformation between the RF interrogator system reference frame and a patient support reference frame; and determine, using the transformation, a second position of the medical device within the patient support reference frame.

In some embodiments, the controller is further configured to control the medical device, using the second position of the medical device within the patient support reference frame, to perform the task with respect to the patient.

In some embodiments, the controller is further configured to determine, using the second position of the medical device, a target position to which to move the medical device in order to perform the task with respect to the patient.

In some embodiments, the controller is further configured to generate a command to cause the medical device to move to the target position in order to perform the task with respect to the patient.

In some embodiments, the medical device comprises an imaging device, and wherein performing the task using the medical device with respect to the patient comprises imaging the patient using the imaging device.

In some embodiments, the medical device comprises a surgical tool, and wherein performing the task using the medical device with respect to the patient comprises treating the patient using the surgical tool.

In some embodiments, the medical device comprises a radiation device, and wherein performing the task using the medical device with respect to the patient comprises irradiating the patient using the radiation device.

In some embodiments, the one or more first RF target devices comprise a first RF target device and a second RF target device, and wherein determining a position of the patient support comprises determining a vector between the RF interrogator system and the first RF target device and a vector between the RF interrogator system and the second RF target device.

In some embodiments, the medical device is a first medical device, and wherein the system further comprises one or more third RF target devices for coupling to a second medical device, wherein the controller is further configured to distinguish an identity of the first medical device from an identity of the second medical device using the received one or more third RF signals.

In some embodiments, the patient support comprises a surgical table or a patient bed.

In some embodiments, the medical device comprises at least one selected from the group consisting of a grasper, forceps, a clamp, an occlude, a drill, a plier, a needle driver, a needle holder, a retractor, a distractor, a positioner, a stereotactic device, a mechanical cutter, a dilators a speculum, a suction tip, a tube, an irrigation needle, an injection needle, a dermatomes, a scope, a probe, a carrier, an applier, a cryotome, a cutting laser guide, a measurement device.

In some embodiments, the one of more first RF signals have a center frequency of 50-70 GHz.

In some embodiments, the one of more second RF signals have a center frequency of 100-140 GHz.

In some embodiments, the controller is configured to determine the transformation by determining a matrix using at least three positions within the RF interrogator system reference frame and at least three positions within the patient support reference frame.

In some embodiments, the controller is configured to determine the transformation prior to controlling the RF interrogator system to transmit one or more first RF signals.

Some embodiments relate to a method performed by a controller part of a system, the system comprising: (i) the controller, (ii) a radio-frequency (RF) interrogator system, (iii) one or more first RF target devices for coupling to a patient support for supporting a patient with respect to whom a medical device is to perform a task, and (iv) one or more second RF target devices for coupling to the medical device. The method comprises, when the one or more first RF target devices are coupled to the patient support and the one or more second RF target devices are coupled to the medical device, using the controller to perform: controlling the RF interrogator system to transmit one or more first RF signals; controlling the RF interrogator system to receive one or more second RF signals transmitted by the one or more first RF target devices responsive to the one or more first RF signals, and one or more third RF signals transmitted by the one or more second RF target devices responsive to the one or more first RF signals; determining, using the received one or more second RF signals, a position of the patient support within an RF interrogator system reference frame; determining, using the received one or more third RF signals, a first position of the medical device within the RF interrogator system reference frame; determining a transformation between the RF interrogator system reference frame and a patient support reference frame; and determining, using the transformation, a second position of the medical device within the patient support reference frame.

In some embodiments, the method further comprises controlling the medical device, using the second position of the medical device within the patient support reference frame, to perform the task with respect to the patient.

In some embodiments, the method further comprises controlling the medical device, using the second position of the medical device within the patient support reference frame, to perform the task with respect to the patient.

In some embodiments, the medical device comprises an imaging device, and wherein performing the task using the medical device with respect to the patient comprises imaging the patient using the imaging device.

In some embodiments, the medical device comprises a surgical tool, and wherein performing the task using the medical device with respect to the patient comprises treating the patient using the surgical tool.

In some embodiments, the medical device comprises a radiation device, and wherein performing the task using the medical device with respect to the patient comprises irradiating the patient using the radiation device.

In some embodiments, the medical device is a first medical device, and wherein the system further comprises one or more third RF target devices for coupling to a second medical device, wherein the method further comprising distinguish an identity of the first medical device from an identity of the second medical device using the received one or more third RF signals.

In some embodiments, determining the transformation comprises determining a matrix using at least three positions within the RF interrogator system reference frame and at least three positions within the patient support reference frame.

Some embodiments relate to a system comprising a radio-frequency (RF) interrogator system; one or more first RF target devices for coupling to a patient support for supporting a patient with respect to whom a medical device is to perform a task; one or more second RF target devices for coupling to the medical device; and a controller. The controller is configured to, when the one or more first RF target devices are coupled to the patient support and the one or more second RF target devices are coupled to the medical device: control the RF interrogator system to transmit one or more first RF signals; control the RF interrogator system to receive one or more second RF signals transmitted by the one or more first RF target devices responsive to the one or more first RF signals, and one or more third RF signals transmitted by the one or more second RF target devices responsive to the one or more first RF signals; determine, using the received one or more second RF signals, a first position of the patient support within an RF interrogator system reference frame; determine, using the received one or more third RF signals, a second position of the medical device within the RF interrogator system reference frame; and determine, using the first and second positions, a target position to which to move the medical device in order to perform the task with respect to the patient.

In some embodiments, the controller is further configured to control the medical device, using the second position of the medical device, to perform the task with respect to the patient at the target location.

In some embodiments, the medical device comprises an imaging device, and wherein performing the task with respect to the patient comprises imaging the patient using the imaging device at the target location.

In some embodiments, the medical device comprises a surgical tool, and wherein performing the task with respect to the patient comprises treating the patient using the surgical tool at the target location.

In some embodiments, the controller is further configured to determine, using information received from a companion localization system, a third position of the medical device within a companion system reference frame; and determine the target position further using the third position.

In some embodiments, the companion system comprises a marker illuminating device; a marker detecting device; and a plurality of reflective markers connected to the medical device. The controller is configured to determine the third position using positions of the plurality of markers.

In some embodiments, the medical device is a first medical device, and the system further comprises one or more third RF target devices for coupling to a second medical device, wherein the controller is further configured to distinguish an identity of the first medical device from an identity of the second medical device using the received one or more third RF signals.

In some embodiments, the target position corresponds to a portion of the patient in need of treatment.

In some embodiments, determining the target position comprises identifying a portion of the patient previously imaged.

Some embodiments relate to a method performed by a controller part of a system, the system comprising: (i) the controller, (ii) a radio-frequency (RF) interrogator system, (iii) one or more first RF target devices for coupling to a patient support for supporting a patient with respect to whom a medical device is to perform a task, and (iv) one or more second RF target devices for coupling to the medical device. The method comprises when the one or more first RF target devices are coupled to the patient support and the one or more second RF target devices are coupled to the medical device, using the controller to perform: controlling the RF interrogator system to transmit one or more first RF signals; controlling the RF interrogator system to receive one or more second RF signals transmitted by the one or more first RF target devices responsive to the one or more first RF signals, and one or more third RF signals transmitted by the one or more second RF target devices responsive to the one or more first RF signals; determining, using the received one or more second RF signals, a first position of the patient support within an RF interrogator system reference frame; determining, using the received one or more third RF signals, a second position of the medical device within the RF interrogator system reference frame; and determining, using the first and second positions, a target position to which to move the medical device in order to perform the task with respect to the patient.

In some embodiments, the method further comprises controlling the medical device, using the second position of the medical device, to perform the task with respect to the patient at the target location.

In some embodiments, the medical device comprises an imaging device, and wherein performing the task with respect to the patient comprises imaging the patient using the imaging device at the target location.

In some embodiments, the medical device comprises a surgical tool, and wherein performing the task with respect to the patient comprises treating the patient using the surgical tool at the target location.

In some embodiments, the method further comprises determining, using information received from a companion localization system, a third position of the medical device within a companion system reference frame; and determining the target position further using the third position.

In some embodiments, determining a third position of the medical device withing the companion system reference frame comprises controlling a marker illuminating device to emit light; and controlling a marker detecting device to detect the light upon reflection from a plurality of reflective markers connected to the medical device.

In some embodiments, the medical device is a first medical device, and wherein the system further comprises one or more third RF target devices for coupling to a second medical device, wherein the method further comprises distinguishing an identity of the first medical device from an identity of the second medical device using the received one or more third RF signals.

In some embodiments, determining the target position comprises identifying a portion of the patient in need of treatment.

In some embodiments, determining the target position comprises identifying a portion of the patient previously imaged.

BRIEF DESCRIPTION OF THE DRAWINGS

Various aspects and embodiments will be described with reference to the following figures. It should be appreciated that the figures are not necessarily drawn to scale. In the drawings, each identical or nearly identical component that is illustrated in various figures is represented by a like numeral. For purposes of clarity, not every component may be labeled in every drawing.

FIG. 5A shows an RF co-localization system configured to use RF localization techniques to facilitate interactions between an imaging device and a patient, in accordance with some embodiments of the technology described herein.

FIG. 7B is a schematic diagram illustrating a surgical tool equipped with reflective markers and one or more target devices, in accordance with some embodiments of the technology described herein.

FIG. 8A is a table illustrating an example of a set of interrogator system parameters, in accordance with some embodiments of the technology described herein.

DETAILED DESCRIPTION

Figure 1A:
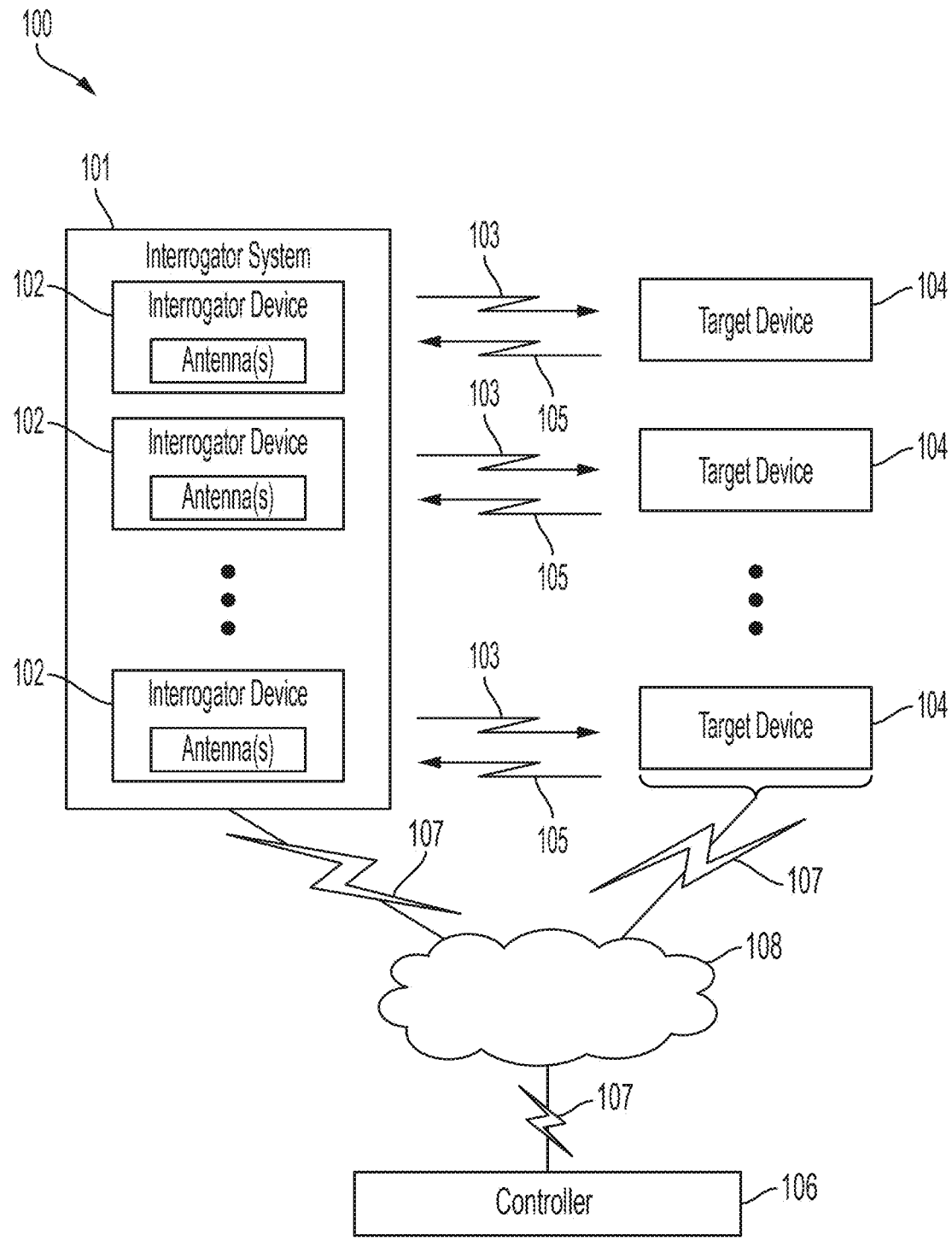
FIG. 1A is a schematic diagram of a system that may be used to implement radio frequency (RF) co-localization techniques, in accordance with some embodiments of the technology described herein.

Determining the position of an object (referred to herein as "localization") has an array of applications in a number of fields. For example, the ability to locate and track an object at very small scales (e.g., at high resolutions) enables numerous applications, and has widespread applicability to a number of different fields. The ability to accurately and precisely determine and track the position (e.g., in one dimension, two dimensions, three dimensions, or according to four degrees of freedom (4 DOF), five degrees of freedom (5 DOF) or six degrees of freedom (6 DOF) of the object including the rotational angles of yaw, pitch, and roll) of an object in real-time has numerous benefits in medical environments (e.g., in a surgical environment, an emergency room, an intensive care unit, a facility where patient procedures are performed, etc.), where medical personnel work, move about, and utilize medical devices (e.g., imaging devices, surgical tools, radiation devices, robotic arms, medication delivery devices, etc.). The performance of certain tasks in such medical environments (e.g., coordinating cooperation among multiple medical devices and a patient during surgical or diagnostic procedures) requires certain accuracy and precision that is not currently available using conventional localization techniques.

Conventional localization techniques have substantial drawbacks and are inadequate for many medical applications and perform unsatisfactorily in all but very limited circumstances or controlled environments. In particular, conventional localization techniques suffer from drawbacks that significantly limit their use and applicability, including manufacturing defects that are difficult to detect, requirement for unique geometries to identify specific objects that often require bulky device attachments, insufficient accuracy and/or precision, low signal-to-noise (SNR) ratio, relatively lengthy refresh rates, susceptibility to background clutter, high cost, and large size. As a result, conventional localization techniques generally have narrow and limited application in medical settings.

Some conventional localization techniques rely on cameras (e.g., infrared cameras), lasers, or other optical systems. These systems have several drawbacks. First, they require an unobstructed line of sight between the object to be localized and the sensing device. Unfortunately, providing an unobstructed line of sight is not always practical in medical settings due to the presence of medical personnel, electronic equipment, medical tools, privacy dividers (e.g., screens), etc. Further, even where a clear line of sight exists, those items can move throughout the duration of a medical procedure (and so can the medical personnel), thus leading to occasional loss of line of sight at times that may be difficult to predict. Second, optical localization systems are susceptible to varying lighting conditions and have trouble detecting overly-shiny or non-reflective components. Therefore, these systems require recalibration to each specific lighting condition. Third, owing to the intrinsic two-dimensional nature of these localization systems, they can determine the position of an object more accurately with respect to transverse directions than they can do with respect to the depth direction (e.g., along the axis that connects the object to be localized to the sensing device).

Other conventional localization systems rely on grid-based simultaneous localization and mapping (SLAM) techniques. However, the performance of these systems typically degrades with changes in the environment (e.g., movement of pieces of equipment, etc.). And such changes are typical in a medical environment (e.g., movement of medical devices, patient support, personnel, etc.), rendering SLAM techniques unsuitable for such applications.

The inventors have developed a radio frequency (RF) based co-localization system for precise and accurate localization of medical devices and patients in a medical environment. In some embodiments, the RF co-localization system operates by using an RF interrogator system and multiple target devices (e.g., transponders) to precisely and accurately estimate positions of medical devices and patients in a common reference frame, which enables the orchestration of multiple tasks in a way that permits precise, safe interactions among medical personnel and medical devices. For example, in some embodiments, an interrogator system may be installed in an environment (e.g., on the ceiling of an operating room), target devices may be coupled to medical devices and to a patient support arranged to support a patient, and the system may be configured to use the interrogator system and the target devices (e.g., by causing the interrogator system to transmit RF signals to and receive responsive RF signals from the target devices) to determine the positions of the target devices in a common reference frame (e.g., the reference frame associated with the interrogator system). The positions so determined provide information about the relative positioning of medical devices with respect to the patient lying on the patient support (thus "co-localizing" them) and, in turn, can be used to control the medical devices to perform a task with respect to the patient.

The systems and techniques developed by the inventors overcome the drawbacks described above in connection with optical localization systems. First, unlike optical rays, RF signals can propagate through certain objects. Therefore, an RF signal can reach a target device notwithstanding the presence of an RF-transparent object obstructing the direct line of sight. Second, unlike their optical counterparts, RF localization systems do not suffer from varying lighting conditions because RF antennas are insensitive to light. Third, some of the RF localization systems developed by the inventors involve ranging techniques, which can provide substantially higher accuracies in the depth direction relative to optical localization systems.

The RF localization techniques developed by the inventors provide a further advantage over conventional localization techniques—they allow for object identification in a reliable fashion regardless of how many target devices need to be identified in a particular environment. Object identification is critically important in localization systems in that they allow a system to obtain a full picture of which particular object of a set of predefined objects is located at which position. This, in turn, allows the system to orchestrate the operations of these objects. In conventional localization techniques, object identification is typically performed on the basis of a geometric characteristic of the object to be localized. Each object exhibits a unique geometric characteristic, which allows the system to distinguish one object from another. However, geometric characteristics can be difficult to spot, especially in poorly-lit environments. Further, this approach requires customization of each object to be localized in an environment so that they can be uniquely identified. Object identification using the RF techniques described herein does not suffer from these limitations because it does not rely on the objects to exhibit different geometric characteristics. Rather, in order to identify an object, the systems described herein rely on a target device affixed to that object to transmit an RF signal to exhibit a particular characteristic. For example, as described in detail further below, some embodiments rely on time-domain identification (according to which each target device transmits an RF signal at a designated time slot of a predefined schedule), code-domain identification (according to which each target device transmits an RF signal that is encoded with a unique code), or frequency-domain identification (according to which each target device transmits an RF signal at a designated center frequency).

The RF localization systems developed by the inventors enable the safe and accurate performance of numerous tasks. For example, as described herein, the RF co-localization system developed by the inventors enables coordination between a medical device (e.g., an imaging device, a surgical tool, a robotic arm, a radiation device, a medication delivery device, etc.) and a patient support arranged to support a patient so that the medical device may perform one or more tasks with respect to the patient. Examples of such tasks include operating the patient, treating the patient with medication, radiation or other therapies, cutting a portion of the patient's body, stitching a portion of the patient body, analyzing a portion of the patient's body, placing a screw or implant in the patient's body, etc.

The systems and techniques described herein allow for the localization of target devices at a distance of approximately 1-6 meters, for example, within a field of view (e.g., conical) of the interrogator system of ±10, 20, 30, 40 or 50 degrees. For example, in some embodiments, localization may be performed within a field of view of ±40 degrees at a range between 1-6 meters, or within a field of view of ±20 degrees at a range of approximately 1-6 meters. In some embodiments, the systems and techniques described herein allow for the localization of target devices at a millimeter resolution (e.g., 1-5 millimeters or 1-10 millimeters).

Figure 8B:
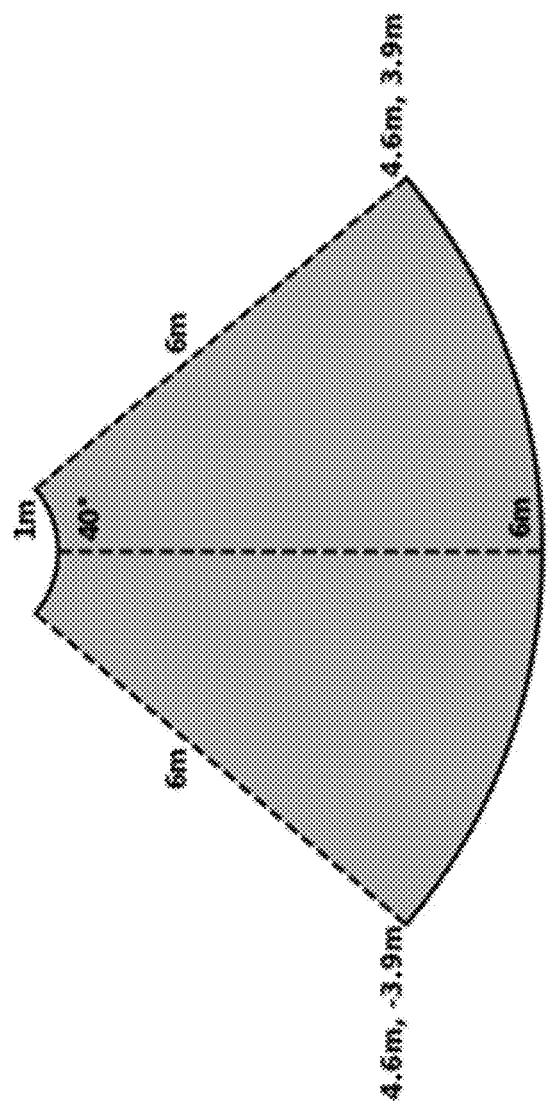
FIG. 8B is a diagram illustrating an example of an interrogator system radiation pattern, in accordance with some embodiments of the technology described herein.

FIG. 8A is a table illustrating an example of a set of interrogator system parameters, in accordance with some embodiments of the technology described herein. In this example, the interrogator exhibits a total update rate of 125 positions per second, a maximum range of 6 meters, a field of view of ±40 degrees, a position precision (at a boresight of ±5 degrees) of ±1 millimeter, a position accuracy (at boresight of ±5 degrees) of ±1 centimeter, a position precision (at a boresight of ±5 degrees to 40 degrees) of ±5 millimeters, a position accuracy (at a boresight of ±5 degrees to 40 degrees) of ±4 centimeters. FIG. 8B is a diagram illustrating an example of an interrogator system radiation pattern, in accordance with some embodiments of the technology described herein. In this example, the radiation diagram exhibits a maximum range of 6 meters and a field of view of ±40 degrees.

The accuracy that can be achieved using the RF localization techniques developed by the inventors can improve the safety and reliability of computer-assisted medical procedures, including robot-assisted surgery, electronic tracking of surgical tools and instruments, remote surgery, targeted radiation therapy, etc.

Accordingly, some embodiments provide for an RF co-localization system. The system includes target devices configured to transmit and receive RF signals. The target devices may include one or more first RF target devices (e.g., 2, 3, 4, or more RF target devices) for coupling to a patient support (e.g., a surgical table or a patient bed). The patient support may be arranged for supporting a patient with respect to whom a medical device (e.g., an imaging device, a surgical tool, a robotic arm, a radiation device, a medication delivery device, etc.) is to perform a task. The target devices may further include one or more second RF target devices for coupling to the medical device.

In some embodiments, the system further includes an interrogator system including RF antennas. The RF antennas may be configured to transmit RF signals to the target devices and receive RF signals from the target devices. In some embodiments, the interrogator system may include RF antennas configured to transmit RF signals and other RF antennas configured to receive RF signals from the target devices, whereas in some embodiments the interrogator system may include RF antennas configured to transmit and receive RF signals. In some embodiments, the target devices may be configured to generate and transmit RF signals in response to receiving RF signals from the interrogator system.

In some embodiments, the system further includes a controller. The controller may be configured to, when the one or more first RF target devices are coupled to the patient support and the one or more second RF target devices are coupled to the medical device, control the RF interrogator system to transmit one or more first RF signals. The controller may be further configured to control the RF interrogator system to receive one or more second RF signals transmitted by the one or more first RF target devices responsive to the one or more first RF signals, and one or more third RF signals transmitted by the one or more second RF target devices responsive to the one or more first RF signals. The controller may be further configured to determine, using the received one or more second RF signals (e.g., using ranging techniques), a position (e.g., location and or orientation) of the patient support within a reference frame associated with the RF interrogator system. The controller may be further configured to determine, using the received one or more third RF signals, a position of the medical device within the reference frame associated with the RF interrogator system. The controller may be further configured to determine a transformation between the reference frame associated with the RF interrogator system and another reference frame that is associated with the patient support. The transformation may be determined, for example, in real time or prior to the beginning of a medical procedure (e.g., prior to transmission of an RF interrogation signal by the RF interrogator system). The transformation may be determined using any suitable algorithm such as, but not limited to, the Kabsch algorithm. The controller may be further configured to determine, using the transformation, a second position of the medical device within the reference frame associated with the patient support.

In one example, the medical device includes an imaging device (e.g., an X-rays imaging device, a magnetic resonance imaging (MRI) device, a computed tomography (CT) scanner, among others) and performing the task involves imaging the patient using the imaging device. In another example, the medical device includes a surgical tool, and performing the task involves treating the patient using the surgical tool. In yet another example, the medical device includes a radiation device, and performing the task involves irradiating the patient using the radiation device.

In some embodiments, the controller is further configured to control the medical device, using the position of the medical device within the reference frame associated with the patient support reference frame, to perform the task with respect to the patient.

In some embodiments, the controller is further configured to determine, using the position of the patient support within the reference frame associated with the patient support reference frame, a target position to which to move the medical device in order to perform the task with respect to the patient. The target position may represent, for example, a particular portion of the body of a patient in need of treatment or a particular portion of the body of a patient to be imaged. In some embodiments, the controller is further configured to generate a command to cause the medical device to move to the target position in order to perform the task with respect to the patient.

In some embodiments, the controller is further configured to distinguish the identity of a medical device from the identify of another medical device using the signal(s) received from the medical device. This may be performed, for example, using time-domain identification, code-domain identification or frequency-domain identification.

As used herein, a position of an item (e.g., a target device, a patient, a patient support, an object, a medical device, etc.) may indicate information describing the location and/or orientation of the item in any suitable coordinate system of any dimension. For example, a position of an item may refer to a one-dimensional (1D) location of the item along a line, an arc or another predefined trajectory, a two-dimensional (2D) location of the item in any suitable 2D coordinate system (e.g., Euclidean, polar, etc.), a three-dimensional (3D) location of the item in any suitable 3D coordinate system (e.g., Euclidean, spherical, cylindrical, etc.), a four-dimensional (4D) position of the item in any suitable 4D coordinate system (e.g., three dimensions for location and one dimension for orientation such as, for example, yaw, pitch, or roll angles), a five-dimensional (5D) position of the item in any suitable 5D coordinate system (e.g., three dimensions for location and two dimension for orientation), or a six-dimensional (6D) position of the item in any suitable 6D coordinate system (e.g., three dimensions for location and three dimensions for orientation).

A medical device may be any device configured to perform or facilitate performance of a task with respect to a patient. Examples of medical devices include imaging devices, surgical tools, robotic arms, radiation devices, and medication delivery devices. A medical device may perform or facilitate performance of a task with respect to a patient in a manual fashion (e.g., by being operated by a user, for example, a surgeon, doctor, radiologist or other medical personnel), in a semi-automatic fashion (e.g., with some level of automation, for example in a user-assisted or user-driven fashion) or in an automatic fashion (e.g., without user intervention).

An imaging device may be any device configured to image a patient. Some imaging devices may include a source configured to produce a field (e.g., radiation, light, acoustic waves, nuclear waves, X-rays, etc.) and a detector configured to sense a portion of the field upon being reflected from a patient. Some imaging devices rely on background light to illuminate the area to be imaged. An imaging device may include a computing system programmed to use the information produced by the detector and to generate an image. Examples of imaging devices include X-rays imaging devices, magnetic resonance imaging (MRI) devices, computed tomography (CT) scanners, fluoroscopic devices, ultrasound devices, echocardiographic devices, positron emission tomography (PET) scanners, cameras, or infrared cameras, among other examples.

A surgical tool may be any tool arranged to perform a task with respect to a patient, including operating, treating, analyzing, deforming, cutting and stitching. Examples of surgical tools include graspers, forceps, clamps, occluders (e.g., for blood vessels or other organs), scissors, bone cutters, saws (unpowered or powered), drills, pliers and pliers-like devices, needle drivers, needle holders, retractors (e.g., used to spread open skin, ribs and other tissues), distractors, positioners, stereotactic devices, mechanical cutters (e.g., scalpels, lancets, trocars, Harmonic scalpel, rongeurs etc.), dilators, specula (e.g., used for access to narrow passages or incisions), suction tips and tubes (e.g., used for removal of bodily fluids), sealing devices (e.g., as surgical staplers), irrigation and injection needles, tips and tubes, powered devices (e.g., such as cranial drills and dermatomes), scopes, probes (e.g., fiber optic endoscopes and tactile probes), carriers and appliers for optical, electronic, and mechanical devices, ultrasound tissue disruptors, cryotomes, cutting laser guides, measurement devices, such as rulers and calipers.

A robotic arm may be any mechanical (e.g., electromechanical) apparatus configured to perform a task with respect to a patient. A robotic arm may operate in an automatic or semi-automatic fashion. A robotic arm may include any suitable type of mechanical arm comprising one or more links connected by joints. A joint may allow rotational motion and/or translational displacement. The links of the arm may be considered to form a chain and the terminus of the chain may be termed an "end effector." A robotic arm may have any suitable number of links (e.g., 1, 2, 3, 4, 5, etc.). For example, a robotic arm may be a multi-axis articulated robot having multiple rotary joints. An end effector may be any suitable terminus of a robotic arm. An end effector may comprise a gripper, a surgical tool, and/or a sensing device. A gripper may be of any suitable type (e.g., jaws or fingers to grasp an object, pins/needles that pierce the object, a gripper operating by attracting an object through vacuum, magnetic, electric, or other techniques). The gripper may be used to grasp an object and to use the object to perform facilitate performance of a task with respect to a patient. A sensing device may be an optical sensor, an electrical sensor, a magnetic sensor, a thermal sensor, or any other suitable sensing device. A sensing device may be used to sense a characteristic of a patient, such as the nature, temperature or composition of a particular tissues. Any one of the surgical tools described above may be coupled to a terminus of a robotic arm.

A radiation device may be any device configured to emit radiation for purposes of performing a task with respect to a patient, such as to treat a patient. Similarly, a medication delivery device may be any device configured to deliver medication for purposes of performing a task with respect to a patient, such as to treat a patient.

Following below are more detailed descriptions of various concepts related to, and embodiments of, techniques for implementing RF co-localization of multiple devices and/or people. It should be appreciated that various aspects described herein may be implemented in any of numerous ways. Examples of specific implementations are provided herein for illustrative purposes only. In addition, the various aspects described in the embodiments below may be used alone or in any combination and are not limited to the combinations explicitly described herein.

FIG. 1A shows a schematic diagram of a system 100 that may be used to implement radio frequency (RF) localization techniques, in accordance with some embodiments of the technology described herein. System 100 comprises an interrogator system 101 including interrogator devices 102 including antenna(s). One or more of the interrogator devices 102 are configured to transmit RF signals 103. System 100 also comprises one or more target devices 104 configured to receive RF signals 103 and, in response, transmit RF signals 105. One or more of the interrogator devices 102 are configured to receive RF signals 105 that are then used to determine distances between the interrogator devices 102 and target devices 104. The computed distances may be used to determine the position of one or more target devices 104. It should be appreciated that while multiple target devices 104 are illustrated in FIG. 1A, a single target device 104 may be utilized. More generally, it should be appreciated that any number of interrogator systems 101, any number of interrogator devices 102, and any number of target devices 104 may be used, as the aspects of the technology described herein are not limited in this respect.

System 100 may also include a controller 106 configured to communicate with interrogator system 101 and target devices 104 via communication channel 108. The communication channel 108 may include a network, device-to-device communication channels, and/or any other suitable means of communication. Controller 106 may be configured to coordinate the transmission and/or reception of RF signals 103 and 105 between desired interrogator and target devices via communication channels 107, which may be a single communication channel or include multiple communication channels. Controller 106 may also be configured to determine the position of one or more target devices 104 from information received from interrogator system 101. As discussed in further detail below, controller 106 may be implemented as a standalone controller or may be implemented in full or in part by one or more interrogator system 101 and/or target devices 104. Different exemplary configurations and implementations for system 100 are described in further detail below but are not limited to the configurations discussed herein.

Resolving the location of a target with a high degree of accuracy depends in part on receiving the RF signals transmitted by the target devices 104 with high fidelity and, in part, on the ability to distinguish the RF signals transmitted by a target device 104 from RF signals transmitted by an interrogator system 101, background clutter, and/or noise. The inventors have developed techniques for improving the signal-to-noise ratio (SNR) of the signals received by the interrogator and target devices to facilitate micro-localization of one or more target devices. As one example, the inventors recognized that by configuring the interrogator and target devices to transmit at different frequencies, localization performance can be improved. According to some embodiments, one or more interrogator systems 101 transmit first RF signals (e.g., RF signals 103) having a first center frequency and, in response to receiving the first RF signals, one or more target devices 104 transmit second RF signals (e.g., RF signals 105) having a second center frequency different from the first center frequency. In this manner, receive antennas on the one or more interrogator systems can be configured to respond to RF signals about the second center frequency, improving the ability of the interrogator systems to receive RF signals from target devices in cluttered and/or noisy environments. According to some embodiments, the second center frequency is harmonically related to the first center frequency. For example, in system 100 illustrated in FIG. 1A, a target device 104 may be configured to transform RF signals 103 and transmit RF signals 105 at a harmonic of the center frequency of the received RF signal 103. In one example, if the center frequency of the RF signal transmitted by an interrogator device were 60 GHz, then the center frequency of the responsive RF signal may be 120 GHz, 180 GHz, or 240 GHz. According to other embodiments, a target device transforms RF signals having a first center frequency received from an interrogator system to RF signals having second center frequency that is different from, but not harmonically related to the first center frequency. In other embodiments, a target device is configured to generate RF signals at a second center frequency different from the first center frequency, either harmonically or not harmonically related, rather than transforming RF signals received from an interrogator system.

The inventors have further recognized that changing the polarization of RF signals transmitted by interrogator and target devices, respectively, may be used to improve SNR and allow interrogator systems to receive RF signals transmitted by target devices with improved fidelity, facilitating micro-localization even in cluttered and/or noisy environments. According to some embodiments, one or more interrogator systems are configured to transmit first RF signals circularly polarized in a first rotational direction (e.g., clockwise) and, in response to receiving the first RF signals, one or more target devices are configured to transmit second RF signals circularly polarized in a second rotational direction different from the first rotational direction (e.g., counterclockwise). A target device may be configured to transform the polarization of received RF signals or may be configured to generate RF signals circularly polarized in the second rotation direction, as aspects of the technology described herein are not limited in this respect. Exemplary techniques for transmitting RF signals, from interrogator and target devices, circularly polarized in different respective rotational directions are discussed in further detail below.

As discussed above, many conventional localization techniques suffer from low SNR and, as a result, are limited in the range in which the localization techniques can operate and/or may exhibit lengthy refresh times (e.g., the interval of time between successive computations of the location of a target) due, at least in part, to the need to repeatedly interrogate the target to build up enough signal to adequately determine the distance to the target. The inventors have developed techniques to improve SNR that substantially increase the range at which micro-localization can be performed (i.e., increase the distance between interrogator and target devices at which the system can micro-locate the target device). Referring again to the exemplary system 100 illustrated in FIG. 1A, an interrogator system 101 may be configured to transmit first RF signals 103 and receive second RF signals 105 transmitted by one or more target devices 104 in response. Accordingly, an interrogator system 101 may comprise interrogator devices 102 including a transmit antenna for transmitting the first RF signals and/or a receive antenna for receiving second RF signals. Any RF signals generated for transmission by and/or transmitted by the interrogator's transmit antenna that are also detected by the interrogator's receive antenna interfere with the ability of the receive antenna to detect RF signals being transmitted by one or more target devices. For example, any portion of an RF signal generated by an interrogator for transmission that is picked up by the interrogator's receive antenna operates as noise that decreases the SNR (or as interference decreasing the SINR, which is the signal to interference plus noise ratio), effectively drowning out the RF signals being transmitted by a target device 104 and reduces the range at which the interrogator can determine the location of the target device.

To increase the SNR, the inventors have developed a number of techniques to reduce the amount and/or impact of signal detection by the receive antenna of RF signals generated by interrogator system for transmission by and/or transmitted by the transmit antenna (or by the transmit antenna of a proximately located interrogator or target devices). As discussed above, transmitting and receiving at different center frequencies facilitate signal differentiation, but also reduces interference between transmit and receive antennas. However, receive antennas remain susceptible to detection of transmitted signals, for example, harmonics that are transmitted from the transmit antenna. The inventors have further recognized that transmitting and receiving at different circular polarizations, as discussed above, further reduces interference between transmit and receive channels. The inventors have further recognized that differentially coupling a receive antenna and/or a transmit antenna to transmit/receive circuitry of the interrogator system reduces the amount of interference between the transmit and receive channels. Similar differential coupling can be implemented at the target device for the same purpose. One or any combination of these techniques may be used to reduce interference and increase SNR.

The inventors have developed numerous techniques that provide for a robust and relatively inexpensive micro-localization system capable of being employed in a wide variety of applications. According to some embodiments, a micro-localization system using techniques described herein are capable of resolving the location of a target device with accuracy in the millimeter or sub-millimeter range in virtually any environment. In addition, using the techniques described herein, location of a target can be determined in milliseconds, a millisecond, or less, facilitating real-time tracking of targets that are rapidly moving. Techniques developed by the inventors, including chip-scale fabrication of micro-localization components, facilitate a general-purpose micro-localization system that can be manufactured at relatively low cost and high volume and that can be conveniently integrated in a variety of application level systems. These and other techniques are discussed in further detail below in connection with exemplary micro-localization systems, in accordance with some embodiments.

Figure 1B:
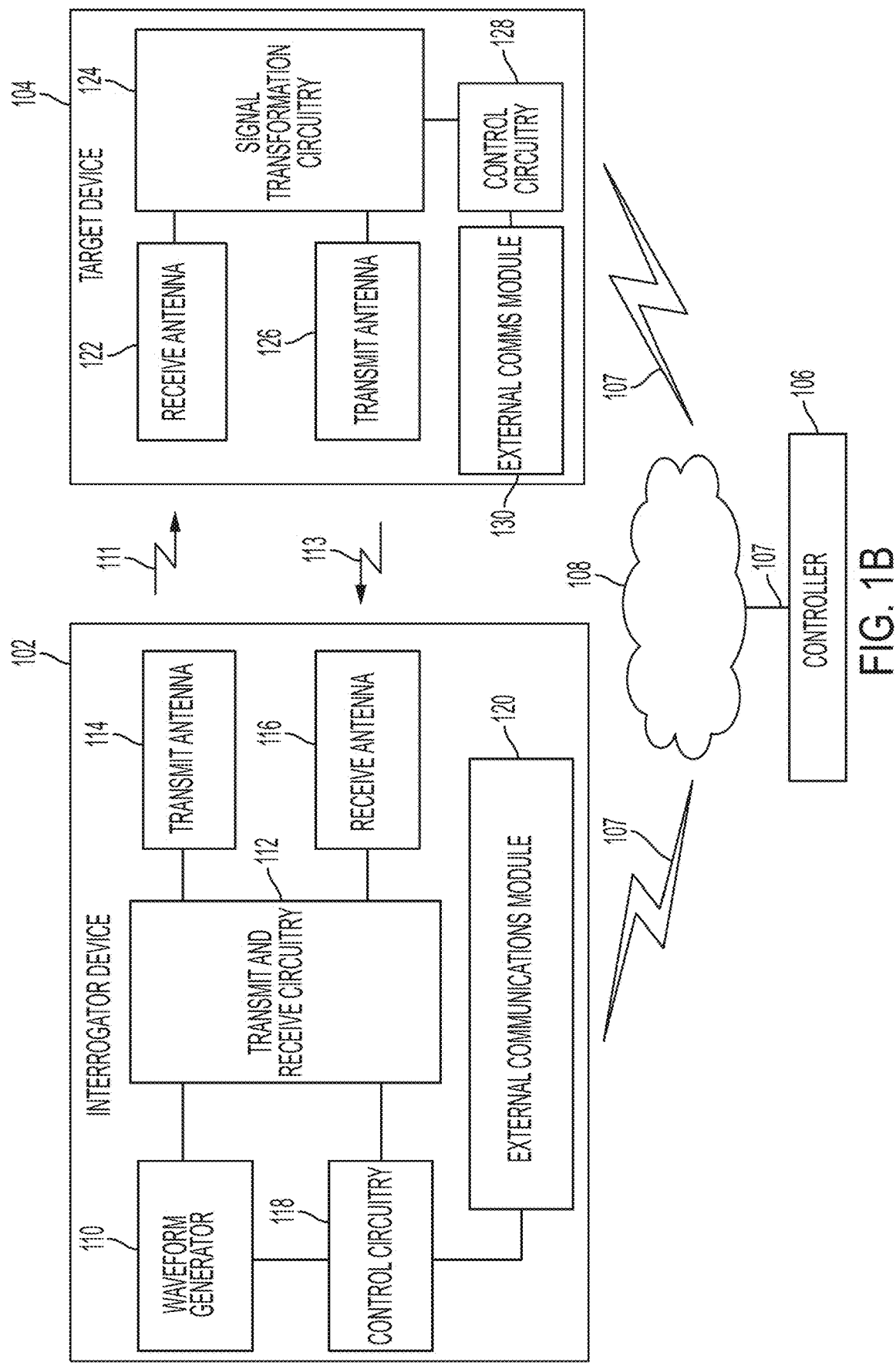
FIG. 1B shows illustrative components of an interrogator device and a target device, which are part of the system shown in FIG. 1A, in accordance with some embodiments of the technology described herein.

FIG. 1B shows illustrative components of an illustrative interrogator device 102 and an illustrative target device 104, which are part of the illustrative system 100 shown in FIG.

1A, in accordance with some embodiments of the technology described herein. As shown in FIG. 1B, illustrative interrogator device 102 includes waveform generator 110, transmit and receive circuitry 112, transmit antenna 114, receive antenna 116, control circuitry 118, and external communications module 120.

It should be appreciated that, in some embodiments, an interrogator device may include one or more other components in addition to or instead of the components illustrated in FIG. 1B. In some embodiments, the interrogator device 102 may include all components as depicted in FIG. 1B (e.g., including the waveform generator 110, control circuitry 118, external communications module 120, and/or transmit and receive circuitry 112). In some embodiments, the interrogator device 102 may share some or all components (e.g., the waveform generator 110, control circuitry 118, external communications module 120, and/or transmit and receive circuitry 112) with other interrogator devices included in the interrogator system to reduce circuitry duplication. Similarly, in some embodiments, a target device may include one or more other components in addition to or instead of the components illustrated in FIG. 1B.

In some embodiments, waveform generator 110 may be configured to generate RF signals to be transmitted by the interrogator device 102 using transmit antenna 114. Waveform generator 110 may be configured to generate any suitable type(s) of RF signals. In some embodiments, waveform generator 110 may be configured to generate frequency modulated RF signals, amplitude modulated RF signals, and/or phase modulated RF signals. Non-limiting examples of modulated RF signals, any one or more of which may be generated by waveform generator 110, include linear frequency modulated signals (also termed "chirps"), non-linearly frequency modulated signals, binary phase coded signals, signals modulated using one or more codes (e.g., Barker codes, bi-phase codes, minimum peak sidelobe codes, pseudo-noise (PN) sequence codes, quadri-phase codes, poly-phase codes, Costas codes, Welti codes, complementary (Golay) codes, Huffman codes, variants of Barker codes, Doppler-tolerant pulse compression signals, impulse waveforms, noise waveforms, and non-linear binary phase coded signals. Waveform generator 110 may be configured to generate continuous wave RF signals or pulsed RF signals. Waveform generator 110 may be configured to generate RF signals of any suitable duration (e.g., on the order of microseconds, milliseconds, or seconds).

In some embodiments, waveform generator 110 may be configured to generate microwave and/or millimeter wave RF signals. For example, waveform generator 110 may be configured to generate RF signals having a center frequency in a given range of microwave and/or millimeter frequencies (e.g., 4-6 GHz, 50-70 GHz). In some embodiments, a target device may transmit a responsive RF signal having a center frequency that is a harmonic of the center frequency of the RF interrogating signal. For example, the responsive signal may have a frequency of 100-140 GHz. It should be appreciated that an RF signal having a particular center frequency is not limited to containing only that particular center frequency (the RF signal may have a non-zero bandwidth). For example, waveform generator 110 may be configured to generate a chirp having a center frequency of 60 GHz whose instantaneous frequency varies from a lower frequency (e.g., 59 GHz) to an upper frequency (e.g., 61 GHz). Thus, the generated chirp has a center frequency of 60 GHz and a bandwidth of 2 GHz and includes frequencies other than its center frequency.

In some embodiments, waveform generator 110 may be configured to generate RF signals using a phase locked loop. In some embodiments, the waveform generator may be triggered to generate an RF signal by control circuitry 118 and/or in any other suitable way.

In some embodiments, transmit and receive circuitry 112 may be configured to provide RF signals generated by waveform generator 110 to transmit antenna 114. Additionally, transmit and receive circuitry 112 may be configured to obtain and process RF signals received by receive antenna 116. In some embodiments, transmit and receive circuitry 112 may be configured to: (1) provide a first RF signal to the transmit antenna 114 for transmission to a target device 104 (e.g., RF signal 111); (2) obtain a responsive second RF signal received by the receive antenna 116 (e.g., RF signal 113) and generated by the target device 104 in response to the transmitted first RF signal; and (3) process the received second RF signal by mixing it (e.g., using a frequency mixer) with a transformed version of the first RF signal. The transmit and receive circuitry 112 may be configured to provide processed RF signals to control circuitry 118, which may (with or without performing further processing the RF signals obtained from transmit and receive circuitry 112) provide the RF signals to external communications module 120.

In some embodiments, each of transmit antenna 114 and receive antenna 116 may be a patch antenna, a planar spiral antenna, an antenna comprising a first linearly polarized antenna and a second linearly polarized antenna orthogonally disposed to the first linearly polarized antenna, a MEMS antenna, a dipole antenna, or any other suitable type of antenna configured to transmit or receive RF signals. Each of transmit antenna 114 and receive antenna 116 may be directional or isotropic (omnidirectional). Transmit antenna 114 and receive antenna 116 may be the same type or different types of antennas.

In some embodiments, transmit antenna 114 may be configured to radiate RF signals circularly polarized in one rotational direction (e.g., clockwise) and the receive antenna 116 may be configured to receive RF signals circularly polarized in another rotational direction (e.g., counter-clockwise). In some embodiments, transmit antenna 114 may be configured to radiate RF signals having a first center frequency (e.g., RF signal 111 transmitted to target device 104) and the receive antenna may be configured to receive RF signals having a second center frequency different from (e.g., a harmonic of) the first center frequency (e.g., RF signal 113 received from target device 104 and generated by target device 104 in response to receiving the RF signal 111).

In some embodiments, transmit antenna 114 and receive antenna 116 are physically separate antennas. In other embodiments, however, the interrogator device 102 may include a dual mode antenna configured to operate as a transmit antenna in one mode and as a receive antenna in another mode.

In some embodiments, control circuitry 118 may be configured to trigger the waveform generator 110 to generate an RF signal for transmission by the transmit antenna 114. The control circuitry 118 may trigger the waveform generator in response to a command to do so received by external communications module 120 and/or based on logic part of control circuitry 118.

In some embodiments, control circuitry 118 may be configured to receive RF signals from transmit and receive circuitry 112 and forward the received RF signals to external communications module 120 for sending to controller 106. In some embodiments, control circuitry 118 may be configured to process the RF signals received from transmit and receive circuitry 112 and forward the processed RF signals to external communications module 120. Control circuitry 118 may perform any of numerous types of processing on the received RF signals including, but not limited to, converting the received RF signals to from analog to digital (e.g., by sampling using an ADC), performing a Fourier transform to obtain a frequency-domain waveform, estimating a time of flight between the interrogator and the target device from the frequency-domain waveform, and determining an estimate of distance between the interrogator device 102 and the target device that the interrogator device 102 interrogated. The control circuitry 118 may be implemented in any suitable way and, for example, may be implemented as an application specific integrated circuit (ASIC), a field programmable gate array (FPGA), a combination of logic circuits, a microcontroller, or a microprocessor.

External communications module 120 may be of any suitable type and may be configured to communicate according to any suitable wireless protocol(s) including, for example, a Bluetooth communication protocol, an IEEE 802.15.4-based communication protocol (e.g., a "ZigBee" protocol), and/or an IEEE 802.11-based communication protocol (e.g., a "WiFi" protocol).

As shown in FIG. 1B, target device 104 includes receive antenna 122, signal transformation circuitry 124, transmit antenna 126, control circuitry 128, and external communications module 130.

In some embodiments, each of receive antenna 122 and transmit antenna 126 may be a patch antenna, a planar spiral antenna, an antenna comprising a first linearly polarized antenna and a second linearly polarized antenna orthogonally disposed to the first linearly polarized antenna, a MEMS antenna, a dipole antenna, or any other suitable type of antenna configured to receive or transmit RF signals. Each of receive antenna 122 and transmit antenna 126 may be directional or isotropic. Receive antenna 122 and transmit antenna 126 may the same type or different types of antennas. In some embodiments, receive antenna 122 and transmit antenna 126 may be separate antennas. In other embodiments, a target device may include a dual mode antenna operating as a receive antenna in one mode and as a transmit antenna in the other mode.

In some embodiments, receive antenna 122 may be configured to receive RF signals circularly polarized in one rotational direction (e.g., clockwise) and the transmit antenna 126 may be configured to transmit RF signals circularly polarized in another rotational direction (e.g., counter-clockwise).

In some embodiments, receive antenna 122 may be configured to receive RF signals having a first center frequency. The received RF signals may be transformed by signal transformation circuitry 124 to obtain transformed RF signals having a second center frequency different from (e.g., a harmonic of) the first center frequency. The transformed RF signals having the second center frequency may be transmitted by transmit antenna 126.

In some embodiments, each of the transmit and/or the receive antennas on an interrogator may be directional antennas. This may be useful in applications where some information is known about the region of space in which the target device is located (e.g., the target device is located in front of the interrogator, to the front left of the interrogator, etc.). Even if the target device is attached to a moving object (e.g., an arm of an industrial robot, a game controller), the movement of the target device may be constrained so that the target device is always within a certain region of space relative to the interrogator so that using directional antennas to focus on that region of space increases the sensitivity of the interrogator to signals generated by the target device. In turn, this increases the distance between the interrogator and target device at which the micro-localization system may operate with high accuracy. However, it should be appreciated that in some embodiments, the antennas on an interrogator may be isotropic (omnidirectional), as aspects of the technology described herein are not limited in this respect.

In some embodiments, each of the transmit and/or the receive antennas on the target device may be isotropic so that the target device may be configured to receive signals from and/or provide RF signals to an interrogator located in any location relative to the target device. This is advantageous because, in some applications of micro-localization, the target device may be moving and its relative orientation to one or more interrogators may not be known in advance. However, in some embodiments, the antennas on a target device may be directional (anisotropic), as aspects of the technology described herein are not limited in this respect.

In some embodiments, control circuitry 128 may be configured to turn the target device 104 on or off (e.g., by powering off one or more components in signal transformation circuitry 124) in response to a command to do so received via external communications module 130. The control circuitry 128 may be implemented in any suitable way and, for example, may be implemented as an application specific integrated circuit (ASIC), a field programmable gate array (FPGA), a combination of logic circuits, a microcontroller, or a microprocessor. External communications module 130 may be of any suitable type including any of the types described herein with reference to external communications module 120.

As discussed above with reference to FIG. 1A, multiple interrogator devices 102 may be utilized in order to determine a location of a target device 104. In some embodiments, at least one of the interrogator devices 102 may be configured to transmit an RF signal to a target device, at least some of the interrogator devices 102 may be configured to receive a responsive RF signal from the target device (the responsive signal may have a different polarization and/or a different center frequency from the signal that was transmitted), and process the transmitted RF signal together with the received RF signal to obtain an RF signal indicative of the distance between the interrogator device and the target device. The RF signals indicative of the distances between the interrogator devices and the target device may be processed (e.g., by the interrogators or another processor) to obtain estimates of the distances between the target device and each of the interrogators. In turn, the estimated distances may be used to determine the position of the target device in a reference frame associated with the interrogator devices.

Figure 1C:
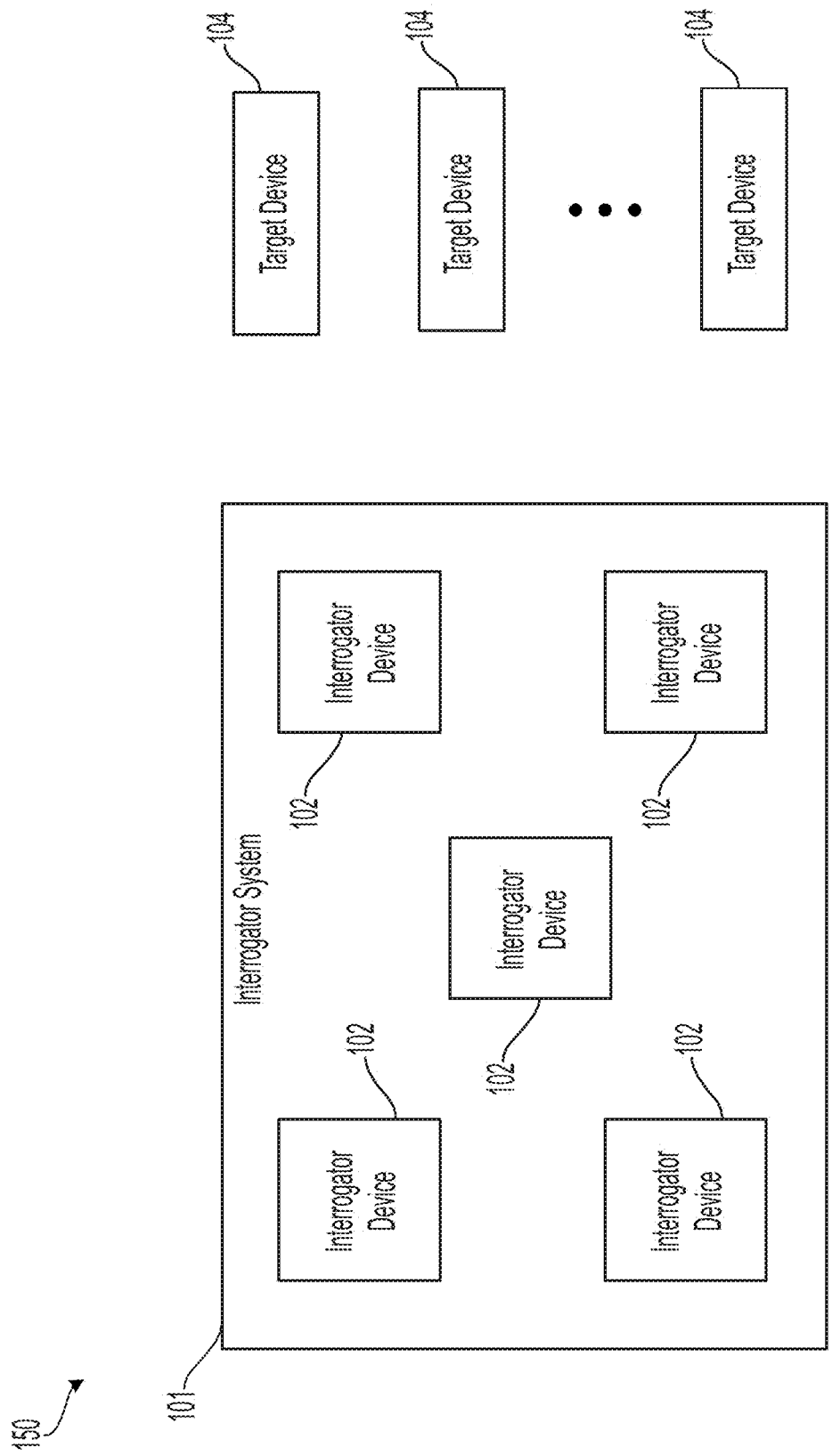
FIG. 1C is a schematic diagram of a system that may be used to implement RF co-localization techniques, in accordance with some embodiments of the technology described herein.

FIG. 1C shows an illustrative system 150 that may be used to implement RF micro-localization techniques, in accordance with some embodiments of the technology described herein. The illustrative system 150 comprises a plurality of interrogator devices 102, which are part of an interrogator system 101. The interrogator devices 102 may be used to obtain estimates of a distance to one or more of the target devices 104. In turn, these distance estimates (e.g., together with the known positions of the interrogators relative to one another) may be used to estimate the position(s) of the target device(s) 104.

Each interrogator device 102 shown in FIG. 1C may be of any suitable type described herein. In some embodiments, the interrogator devices 102 may be of the same type of interrogator device. In other embodiments, at least two of these interrogator devices may be of different types. Some or all the interrogator devices 102 may be designed as described in connection with FIG. 1B, though in some embodiments, some of the components (e.g., waveform generator 110, control circuitry 118, external communications module 120 and/or transmit and receive circuitry 112) may be shared among multiple interrogator devices 102.

Although there are five interrogator devices shown as part of interrogator system 101, in other embodiments, any other suitable number of interrogators may be used (e.g., one, two, three, four, six, seven, eight, nine, ten, etc.), as aspects of the technology described herein are not limited in this respect. For example, in some embodiments, one interrogator device 102 may be configured to transmit RF signals to a target device 104 and receive RF signals from the same target device, whereas the other interrogator devices 102 may be receive-only interrogators configured to receive RF signals from the target device 104, but which are not capable of transmitting RF signals to target device 104 (e.g., because these interrogators may not include transmit circuitry for generating RF signals for transmission by a transmit antenna and/or the transmission antenna). It should also be appreciated that each of target devices 104 may be of any suitable type(s) described herein, as aspects of the technology described herein are not limited in this respect.

Figure 1D:
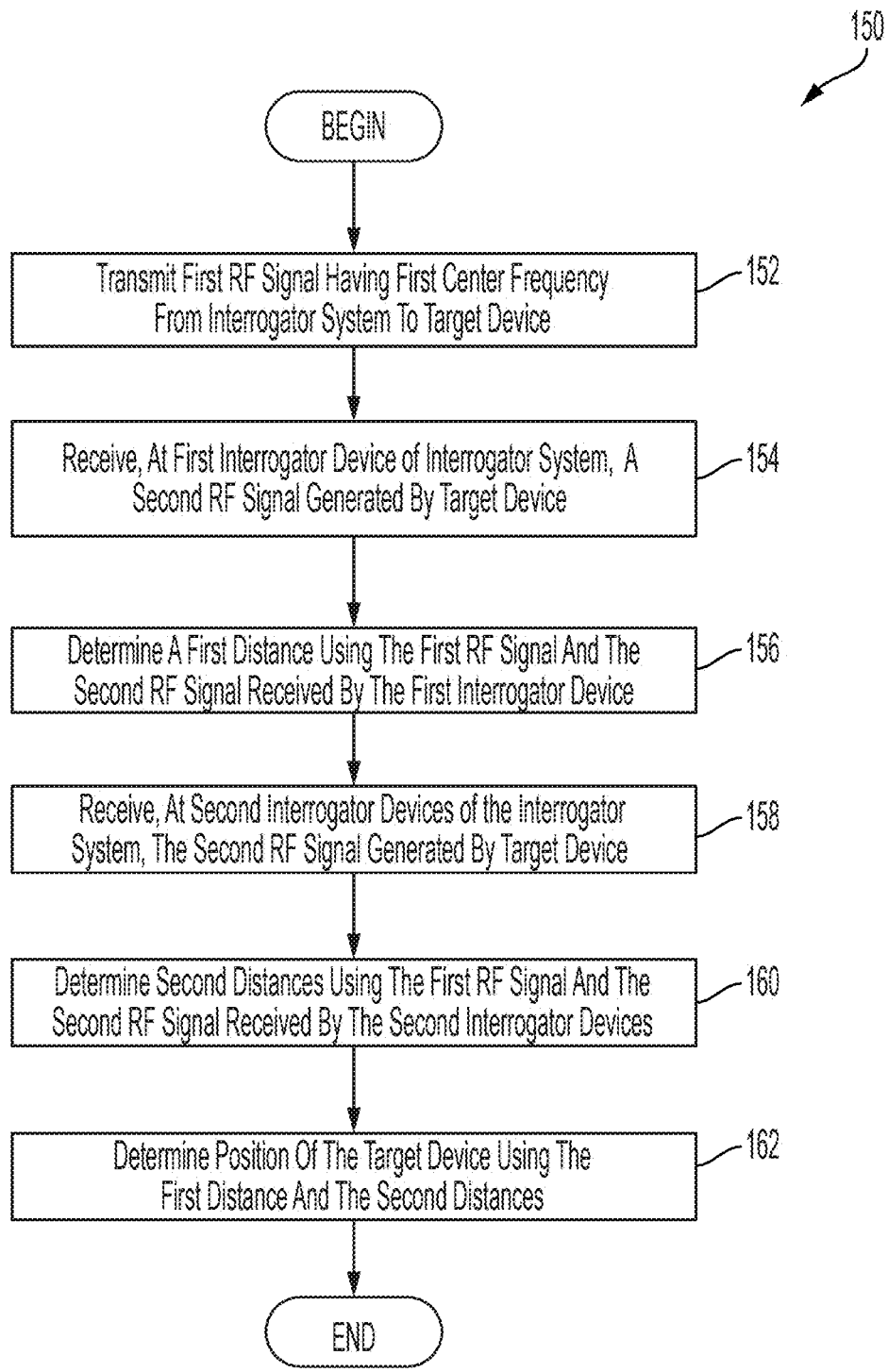
FIG. 1D is a flowchart of a process for determining the location of a target device using measurements made by an interrogator system, in accordance with some embodiments of the technology described herein.

FIG. 1D is a flowchart of an illustrative process 150 for determining the location of a target device using measurements made by an interrogator system including two receive antennas, in accordance with some embodiments of the technology described herein. Process 150 may be executed by any suitable localization system described herein including, for example, system 100 described with reference to FIG. 1A.

Process 150 begins at act 152, where the interrogator system transmits a first RF signal having a first center frequency to a target device. For example, the interrogator system 101 may send RF signal 103 to target device 104. The RF signal may be of any suitable type and, for example, may be a linear frequency modulated RF signal or any other suitable type of RF signal including any of the types of signals described herein. The first RF signal transmitted at act 152 may have any suitable center frequency. For example, the center frequency may be any frequency in the range of 50-70 GHz (e.g., 60 GHz) or any frequency in the range of 4-6 GHz (e.g., 5 GHz). The first RF signal transmitted at act 152 may be circularly polarized in the clockwise or counterclockwise direction.

At act 154, the first interrogator system that, at act 152, transmitted an RF signal to a target device, may receive a responsive second RF signal from the target device at a first interrogator device. For example, a first interrogator device 102 of the interrogator system 101 may receive second RF signal 105 from target device 104. The responsive second RF signal may be a transformed version of the transmitted first RF signal. The target device may generate the responsive RF signal by receiving and transforming the transmitted RF signal according to any of the techniques described herein.

In some embodiments, the frequency content of the responsive second RF signal received at act 154 may be different from that of the transmitted RF signal transmitted at act 152. For example, when the transmitted RF signal has a first center frequency, the responsive RF signal may have a second center frequency different from the first center frequency. For example, the second center frequency may be a harmonic of the first center frequency (e.g., the second center frequency may be an integer multiple of, such as twice as, the first center frequency). As one example, if the center frequency of the transmitted first RF signal were 60 GHz, then the center frequency of the responsive second RF signal may be 120 GHz, 180 GHz, or 240 GHz. In some embodiments, the polarization of the responsive second RF signal may be different from the polarization of the transmitted first RF signal. For example, when the transmitted first RF signal is circularly polarized in a clockwise direction, the received second RF signal may be circularly polarized in a counter-clockwise direction. Alternatively, when the transmitted first RF signal is circularly polarized in a counter-clockwise direction, the received second RF signal may be circularly polarized in a clockwise direction.

At act 156, an estimate of the distance between the first interrogator device of the interrogator system and the target device may be determined by using the first RF signal transmitted at act 152 and the second RF signal received at act 154. This may be done in any suitable way. For example, in some embodiments, the first and second RF signals may be mixed (e.g., using a frequency mixer onboard the first interrogator device) to obtain a mixed RF signal. The mixed RF signal may be indicative of the time-of-flight and, consequently, the distance between the first receive antenna and the target device. The mixed RF signal may be sampled (e.g., using an ADC) and a Fourier transform (e.g., a discrete Fourier transform, a fast Fourier transform) may be applied to the samples to obtain a frequency-domain waveform. The frequency-domain waveform may be processed to identify the time-of-flight of an RF signal between the first receive antenna and the target device. In some embodiments, the frequency-domain waveform may be processed to identify the time-of-flight by identifying a first time when a responsive RF signal generated by the target device is detected by the first receive antenna of the interrogator device. This may be done in any suitable way. For example, the frequency-domain waveform may include multiple separated "peaks" (e.g., multiple Gaussian-like bumps each having a respective peak above the noise floor) and the location of the first such peak may indicate the first time when the responsive RF signal generated by the target is detected by the first receive antenna of the interrogator device. This first time represents an estimate of the time-of-flight between the first receive antenna and target device. In turn, the estimate of the time-of-flight between the first receive antenna and the target device may be converted to an estimate of the distance between the first receive antenna and the target device.

Accordingly, in some embodiments: (1) an interrogator system may transmit an RF signal to a target device and receive at a first interrogator device, from the target device, a responsive RF signal; (2) a version of the transmitted RF signal may be mixed with the received RF signal to obtain a mixed RF signal; (3) the mixed RF signal may be sampled using an ADC to obtain a sampled signal; (4) the sampled signal may be transformed by a discrete Fourier transform to obtain a frequency-domain waveform; (5) the frequency-domain waveform may be processed to identify the time-of-flight between the first interrogator device and the target device; and (6) the time-of-flight may be converted to an estimate of the distance between the first interrogator device and the target device.

It should be appreciated that while all of these acts 1-6 may be performed on a single device (e.g., the interrogator system), this is not a limitation of aspects of the technology described herein. For example, in some embodiments, an interrogator system may not include an ADC, and steps 3-6 may be performed by one or more devices external to an interrogator system. Even in embodiments where the interrogator system includes an ADC, the acts 4-6 may be performed by one or more device (e.g., a processor) external to the interrogator system.

At act 158, the first interrogator system that, at act 152, transmitted an RF signal to a target device, may receive the responsive second RF signal from the target device at second interrogator devices different than the first interrogator device.

At act 160, an estimate of the distances between the second interrogator devices and the target device may be determined by using the received second RF signal received by the second interrogator devices at act 158. This may be done in any suitable way including in any of the ways described above with reference to act 156.

At act 162, the position of the target device may be determined using the distance between the first interrogator device and the target device obtained at act 156, the distances between the second interrogator devices and the target device obtained at act 160, and known locations of the first and second interrogator devices. This determination may be made in any suitable way and, for example, may be made using any of numerous types of geometric methods, least-squares methods, trilateration methods, and/or in any of the ways described in U.S. Pat. No. 10,591,592 titled "High-Precision Time of Flight Measurement Systems," filed on Jun. 14, 2016, U.S. Patent Publication No. 2016/0363648 titled "High Precision Motion Tracking with Time of Flight Measurement Systems," filed on Jun. 14, 2016, U.S. Patent Publication No. 2016/0363664 titled "High Precision Subsurface Imaging and Location Mapping with Time of Flight Measurement Systems," filed on Jun. 14, 2016, and U.S. Patent Publication No. 2016/0363663 titled "High-Precision Time of Flight Measurement System for Industrial Automation," filed on Jun. 14, 2016, and in "Closed-form algorithms in mobile positioning: Myths and misconceptions," N. Sirola, 2010 7th Workshop on Positioning, Navigation and Communication, 2010, pp. 38-44, each of which is herein incorporated by reference in its entirety.

It should be appreciated that process 150 is illustrative and that there are variations. For example, in some embodiments, more than two receive antennas or more than two interrogator devices may be used to interrogate a single target device. In such embodiments, estimates of distances between the target device and each of the three or more receive antennas and/or interrogator devices may be used to obtain the two-dimensional position of the target devices (e.g. to specify a two-dimensional plane containing the three-dimensional target devices). When distances between at least three receive antennas and/or interrogator devices and a target device are available, then the three-dimensional position of the target device may be determined. Additional aspects of associated technology for performing RF localization are described in U.S. Pat. No. 10,094,909 titled "Radio-Frequency Localization Techniques and Associated Systems, Devices, and Methods," filed on Jul. 28, 2017, which is herein incorporated by reference in its entirety.

Figure 2A:
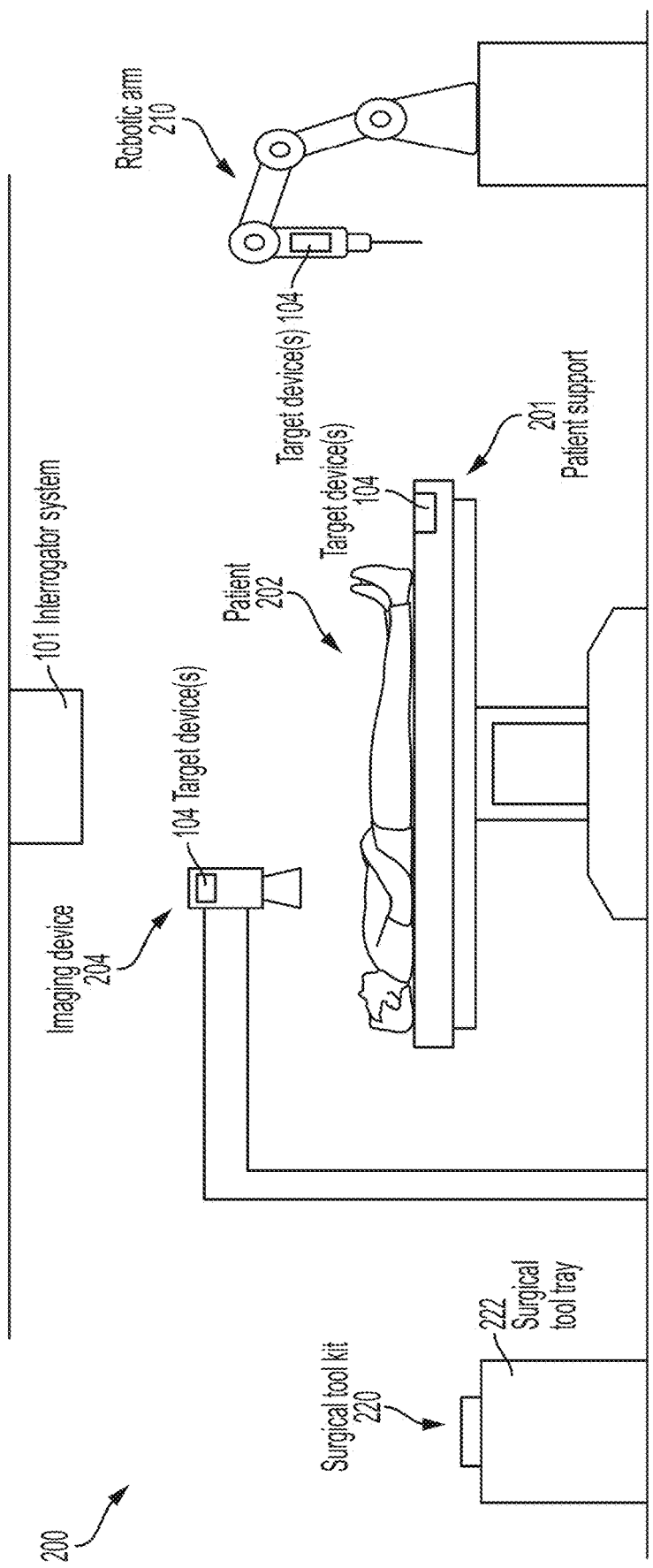
FIG. 2A shows an RF co-localization system configured to use RF localization techniques to facilitate interactions between a medical device and a patient, in accordance with some embodiments of the technology described herein.

FIG. 2A shows an RF co-localization system 200 configured to use RF localization techniques to facilitate interactions between one or more medical devices and a patient 202, in accordance with some embodiments of the technology described herein. The RF co-localization system 200 includes an interrogator system 101 (e.g., interrogator system 101 as described in connection with FIGS. 1A-1D) disposed above the environment in which patient 202 is positioned. For example, the interrogator system 101 may be coupled to the ceiling or other support structure above or adjacent the environment. The environment may be any suitable type of medical setting, including for example an emergency room, an intensive care unit, an operating room, a delivery room, a triage room, etc. The environment may be organized, for example, to allow medical personnel to analyze, diagnose, image, treat or operate patients. The RF co-localization system 200 further includes target devices 104 (e.g., target devices 104 as described in connection with FIGS. 1A-1D) positioned at various locations of the environment, as described in detail further below.

As shown in FIG. 2A, a patient 202 is supported by a patient support 201. Patient support 201 may be, for example, a surgical table, a patient bed, a chair (e.g., a dental chair unit) a stool, or any other suitable type of patient support. More generally, a patient support may be arranged (e.g., shaped and sized) to support a patient or a portion of a patient's body thereon. Patient support 201 may be stationary (e.g., permanently or temporarily fixed in position) or movable (e.g., may have wheels and/or may be coupled to a movable platform or other mechanisms). A patient support may be moved manually within an environment. Additionally, or alternatively, a movable platform may be an automatically-positioned support configured to move throughout the environment autonomously, or with the assistance of a user.

In some embodiments, a patient support 201 may include one or more target devices 104. The target device(s) 104 may be, for example, affixed to known location(s) of patient support 201. In some embodiments, in order to facilitate the determination of the orientation of a patient support, at least some of the target devices may be disposed on the patient support in accordance with a predefined arrangement. Controller 106 may determine the position(s) of target device(s) 104 in the reference frame of the interrogator system 101, for example as described in connection with FIGS. 1A-1D. Consequently, controller 106 may determine the position (e.g., location and/or orientation) of patient support 201, such as the position of a particular portion of the patient support (e.g., a corner of the patient support or the portion of the patient support where the patient is expected to rest a particular body part). Depending on the number of target devices that patient support 201 includes, the controller can determine the position of the patient support in 1D, 2D, 3D, 4D, 5D and 6D. In some embodiments, it is presumed that, once a patient 202 is supported by a patient support 201, the patient does not move with respect to the patient support. In these embodiments, the position of the patient can be inferred directly from the position of the patient support. However, in some embodiments, the patient may be moved relative to the patient support. For example, the patient may be flipped or rotated and may not return to the original position on the patient support. In these embodiments, in order to determine the position of a particular portion of the patient body, the system should take into account the extent to which the patient has moved from the original position. In some embodiments, this may be achieved by placing target devices directly on or inside the patient, at least for the duration of the medical procedure. For example, one or more posts may be affixed to a portion of the patient's body, and target devices may be positioned on such post(s).

The environment may include one or more medical devices. For example, the environment may include one or more of the following medical devices: imaging device 204, robotic arm 210, surgical tool kit 220, a radiation device (not shown in FIG. 2A), a medication delivery device (not shown in FIG. 2A), etc.

In some embodiments, the imaging device 204 may be mounted on an apparatus having a cavity (e.g., a cylindrical cavity) formed therethrough. The cavity may be sized to allow patient support 201 to slide therein using a motorized mechanism, thereby allowing the imaging device to scan the patient. In some embodiments, imaging device 204 is stationary (e.g., permanently or temporarily fixed in position) and patient support 201 is movable. In other embodiments, imaging device 204 is movable and patient support 201 is stationary. In yet other embodiments, both imaging device 204 and patient support 201 are movable. An imaging device may be mounted on a mechanism designed to move the imaging device around an environment. In one example, an imaging device may be mounted on a rail allowing for motion of the imaging device along a line, an arc, or other predefined trajectories. In another example, an imaging device may be mounted on a mechanism allowing for motion in two dimensions (e.g., two dimensions for location, one dimension for location and one dimension for orientation or two dimensions for orientation), in three dimensions (e.g., three dimensions for location, two dimensions for location and one dimension for orientation, one dimension for location and two dimensions for orientation or three dimensions for orientation), in four dimensions (e.g., three dimensions for location and one dimension for orientation, two dimensions for location and two dimensions for orientation, or one dimension for location and three dimensions for orientation), in five dimensions (e.g., three dimensions for location and two dimensions for orientation, two dimensions for location and three dimensions for orientation), or in six dimensions (e.g., three dimensions for location and three dimensions for orientation).

An imaging device 204 may include one or more target devices 104. The target device(s) 104 may be, for example, affixed to known location(s) of imaging device 204. In some embodiments, in order to facilitate the determination of the orientation of a medical device, at least some of the target devices may be disposed on the medical device in accordance with a predefined arrangement. Controller 106 may determine the position(s) of target device(s) 104 in the reference frame of the interrogator system 101, for example as described in connection with FIGS. 1A-1D. Consequently, controller 106 may determine the position (e.g., location and/or orientation) of imaging device 204, such as the position of a particular portion of imaging device 204 (e.g., the detector of imaging device 204 or the portion of imaging device 204 from which the viewpoint of the images produced by the imaging device is established). Depending on the number of target devices that imaging device 104 includes, the controller can determine the position of the imaging device in 1D, 2D, 3D, 4D, 5D and 6D. In one example, controller 106 may determine the position of imaging device 204 along a predefined trajectory (e.g., along a predefined line or a predefined arc). In this example, imaging device 204 may include one or more target devices. In another example, controller 106 may determine the position of imaging device 204 along a predefined trajectory, and the orientation of imaging device 204 with respect to one, two or three rotational angles (e.g., yaw, pitch, roll or any combinations thereof). In this example, imaging device 204 may include two or more target devices. In another example, controller 106 may determine the position of imaging device 204 in a predefined plane. In this example, imaging device 204 may include two or more target devices. In another example, controller 106 may determine the position of imaging device 204 in a predefined plane, and the orientation of imaging device with respect to one, two or three rotational angles (e.g., yaw, pitch, roll or any combinations thereof). In this example, imaging device 204 may include two or more target devices. In another example, controller 106 may determine the position of imaging device 204 in 3D. In this example, imaging device 204 may include three or more target devices. In another example, controller 106 may determine the position of imaging device 204 in 3D, and the orientation of imaging device with respect to one, two or three rotational angles (e.g., yaw, pitch, roll or any combinations thereof). In this example, imaging device 204 may include four or more target devices.

In some embodiments, imaging device 204 may include more target devices than would be necessary to determine the location of the imaging device. Some such target devices may be used for redundancy. In some embodiments, for example, the line of sight between an interrogator device and a target device may be obstructed when the imaging device is in a particular position. As a result, communication between the interrogator device and the target device may be noisy, thus potentially leading to errors. To obviate this issue, an imaging device may be equipped with additional target device(s). The additional target device(s) may be positioned so that there is at least one interrogator device/target device pair with an unobstructed line of sight.

Figure 2B:
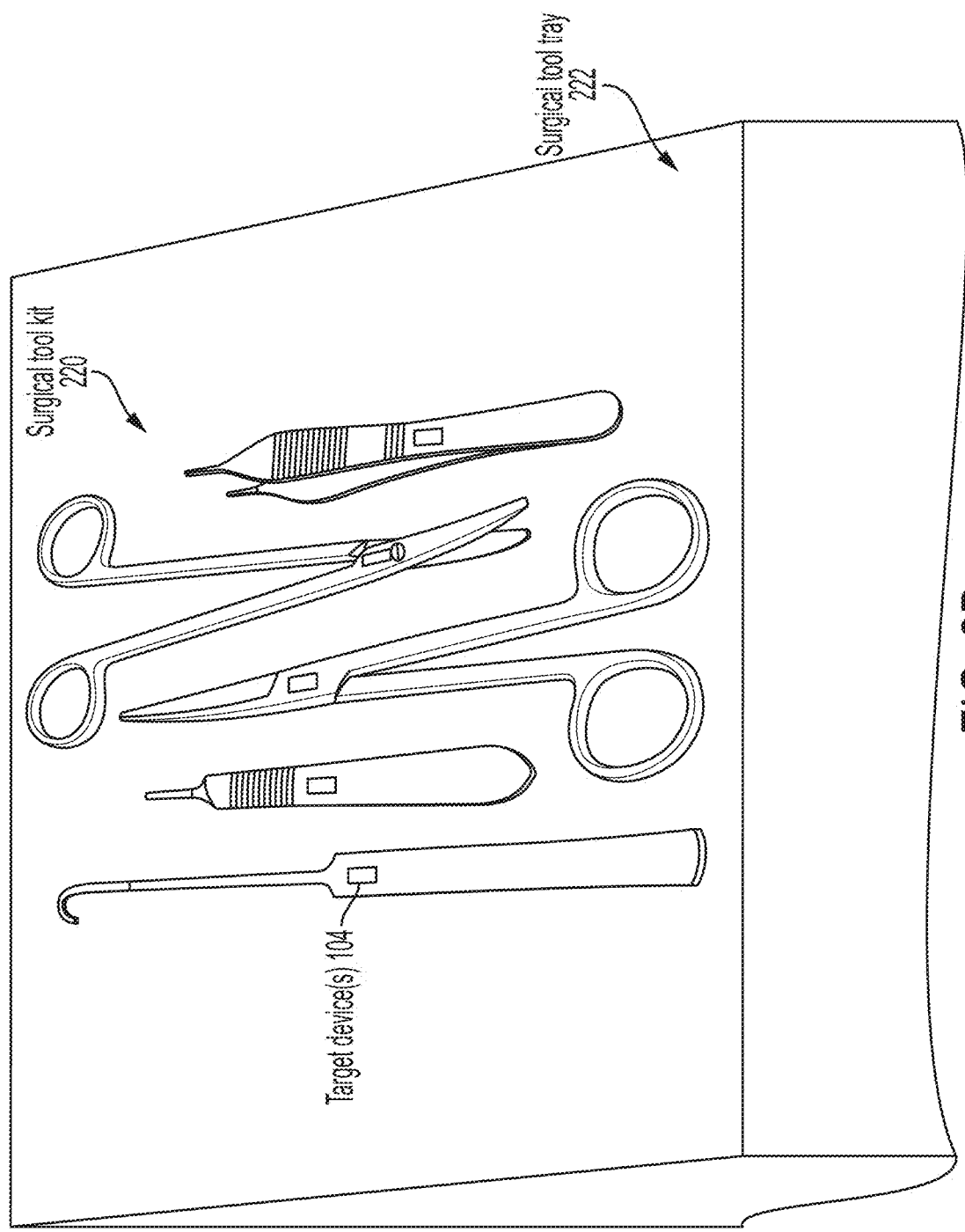
FIG. 2B shows a surgical tool kit, where each tool includes a target device for localization, in accordance with some embodiments of the technology described herein.

Surgical tool kit 220 may include one or more surgical tools, as shown in further detail in FIG. 2B, in accordance with some embodiments of the technology described herein. Surgical tool kit 220 may be disposed on top of a surgical tool tray 222. Each (or at least some) surgical tool of the kit may include one or more target devices 104. Controller 106 may determine the position(s) of these target device(s) 104 in the reference frame of the interrogator system 101, for example as described in connection with FIGS. 1A-1D. Consequently, controller 106 may determine the position (e.g., location and/or orientation) of the surgical tools, such as the position of a particular portion of a surgical tool (e.g., the tip of a surgical tool). Depending on the number of target devices that a surgical tool includes, the controller can determine the position of the surgical tool in 1D, 2D, 3D, 4D, 5D and 6D. A surgical tool may include additional target devices for redundancy.

Referring back to FIG. 2A, robotic arm 210 may include one or more target devices 104. Controller 106 may determine the position(s) of these target device(s) 104 in the reference frame of the interrogator system 101, for example as described in connection with FIGS. 1A-1D. Consequently, controller 106 may determine the position (e.g., location and/or orientation) of the robotic arm, such as the position of a particular portion of the robotic arm (e.g., the terminus of the robotic arm). Depending on the number of target devices that a surgical tool includes, the controller can determine the position of the surgical tool in 1D, 2D, 3D, 4D, 5D and 6D. Robotic arm 210 may include additional target devices for redundancy.

Figure 3A:
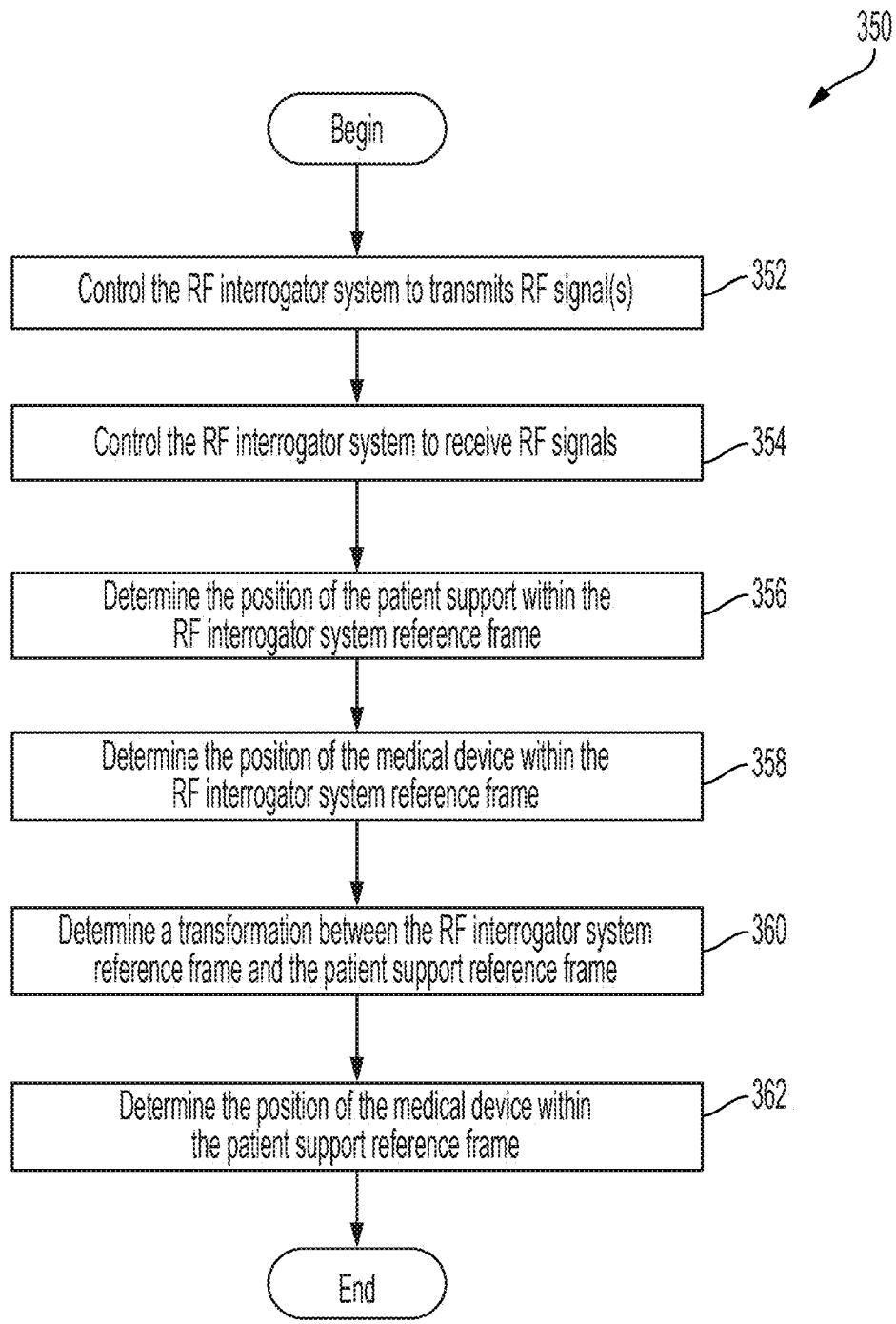
FIG. 3A is a flowchart illustrating a process for co-localization of medical devices and a patient support, in accordance with some embodiments of the technology described herein.
Figure 3B:
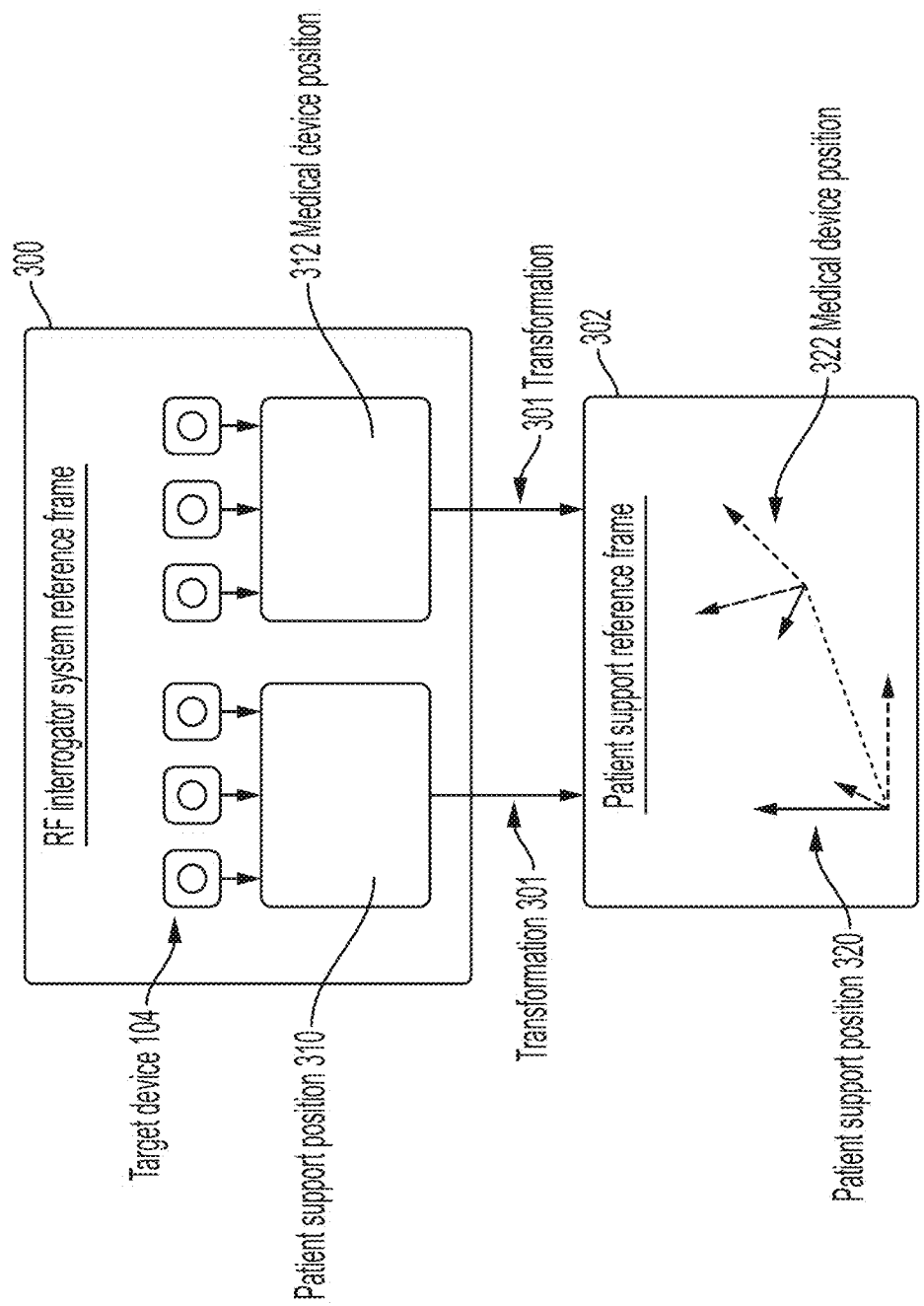
FIG. 3B is a schematic diagram illustrating an RF interrogator system reference frame and a patient support reference frame, in accordance with some embodiments of the technology described herein.

In some embodiments, the environment may include a radiation emitting device including one or more target devices. In some embodiments, the environment may include a medication delivery device including one or more target devices. Depending on the number of target devices that these medical devices include, the controller can determine the position of the medical device in 1D, 2D, 3D, 4D, 5D and 6D. The operation of the RF co-localization system 200 will be described herein with reference to FIGS. 3A-3B, in accordance with some embodiments of the technology described herein. FIG. 3A is a flowchart illustrating a process 350 for co-localization of a medical device and a patient. FIG. 3B is a schematic diagram illustrating the positions of a medical device and a patient support with respect to an RF localization system reference frame and a patient support reference frame. Process 350 begins at act 352, where a controller controls an interrogator system to transmit one or more RF signals. Referring for example to FIG. 1A, a controller 106 may control an interrogator system 101 to transmit one or more RF signals. For example, controller 106 may cause an interrogator device 102 to drive a current through an antenna, thereby causing the antenna to emit RF radiation. When multiple RF signals are transmitted, these signals may be transmitted by the same interrogator device 102, or by different interrogator devices 102. The transmitted RF signal(s) may be transmitted in a direction so as to hit the target device(s) of interest. For example, one RF signal may be transmitted in the direction of the target device of a patient support 201 and another RF signal may be transmitted in the direction of a target device of an imaging device 204. In another example, an interrogator system may transmit with a sufficiently wide field of view so as to interrogate several target devices with the same RF signal or the same RF signals. In some embodiments, responsive to the RF signal(s) transmitted by interrogator system 101, one or more target devices may in turn transmit RF signals. For example, the target device(s) of a patient support 201 may transmit RF signals responsive to a first RF signal transmitted by the interrogator device, and the target device(s) of a medical device (e.g., imaging device 204, robotic arm 210, one of the surgical tools of kit 220, etc.) may transmit RF signals responsive to a second RF signal transmitted by the interrogator device. In another example, the target device(s) of a patient support and the target device(s) of a medical device may transmit RF signals responsive to the same RF signal transmitted by the interrogator device. The target devices may transmit response signals simultaneously or in accordance with a predefined schedule so that the interrogation system receives different response signals at different times (which in some embodiments allows the interrogation system to distinguish medical devices from one another). It should be appreciated that not all the target devices of a patient support or a medical device may transmit, as some of these target devices may be angled in such a way as to not receive an interrogating signal, for example because the line of sight may be obstructed.

At act 354, the controller controls the interrogator system to receive the RF signals transmitted by the target device(s) of a patient support. Further, the controller controls the interrogator system to receive the RF signals transmitted by the target device(s) of a medical device. In some embodiments, controlling an interrogator system to receive an RF signal involves causing the interrogator system to detect (optionally, amplify) and digitize the current produced by an antenna or the currents produced by multiple antennas.

At act 356, the controller determines the position (e.g., location and/or orientation) of the patient support 201 using the RF signal(s) transmitted by the target device(s) of the patient support. Depending on how many target devices are included in the patient support, the controller may determine the position of the patient support in 1D, 2D, 3D, 4D, 5D or 6D. Determining the position of the patient support may be performed using any of the techniques described in connection with FIGS. 1A-1D. For example, this may be performed by determining the vector between an interrogator device and a target device. Such a vector may include the distance between the interrogator device and the target device and/or the orientation of the target device relative to the interrogator device. Determining a 1D position of a patient support may involve determining a location along a line, an arc or another predefined trajectory. Determining a 2D position of a patient support may involve determining a location in a 2D coordinate system (e.g., Euclidean, polar, etc.), a location in a 1D coordinate system and an orientation with one angular degree of freedom (e.g., one among pitch, roll and yaw) or an orientation with two angular degrees of freedom (two among pitch, roll and yaw). Determining a 3D position of a patient support may involve determining a location in a 3D coordinate system (e.g., Euclidean, spherical or cylindrical, etc.), a location in a 2D coordinate system and an orientation with one angular degree of freedom (e.g., one among pitch, roll and yaw), a location in a 1D coordinate system and an orientation with two angular degrees of freedom (e.g., two among pitch, roll and yaw) or an orientation with three angular degrees of freedom (pitch, roll and yaw). Determining a 4D position of a patient support may involve determining a location in a 3D coordinate system and an orientation with one angular degree of freedom, a location in a 2D coordinate system and an orientation with two angular degrees of freedom, a location in a 1D coordinate system and an orientation with three angular degrees of freedom. Determining a 5D position of a patient support may involve determining a location in a 3D coordinate system and an orientation with two angular degrees of freedom or a location in a 2D coordinate system and an orientation with three angular degrees of freedom. Determining a 6D position of a patient support may involve determining a location in a 3D coordinate system and an orientation with three angular degrees of freedom.

At act 358, the controller determines the position of a medical device using the RF signal(s) transmitted by the target device(s) of the medical device (although in some embodiments the positions of more than one medical device may be determined at act 358). Depending on how many target devices are included in the medical device, the controller may determine the position of the medical device in 1D, 2D, 3D, 4D, 5D or 6D. Determining the position of the medical device may be performed using any of the techniques described in connection with FIGS. 1A-1D. For example, this may be performed by determining the vector between an interrogator device and a target device. Such a vector may include the distance between the interrogator device and the target device and/or the orientation of the target device relative to the interrogator device. Determining a 1D position of a medical device may involve determining a location along a line, an arc or another predefined trajectory. Determining a 2D position of a medical device may involve determining a location in a 2D coordinate system, a location in a 1D coordinate system and an orientation with one angular degree of freedom or an orientation with two angular degrees of freedom. Determining a 3D position of a medical device may involve determining a location in a 3D coordinate system, a location in a 2D coordinate system and an orientation with one angular degree of freedom, a location in a 1D coordinate system and an orientation with two angular degrees of freedom or an orientation with three angular degrees of freedom. Determining a 4D position of a medical device may involve determining a location in a 3D coordinate system and an orientation with one angular degree of freedom, a location in a 2D coordinate system and an orientation with two angular degrees of freedom, a location in a 1D coordinate system and an orientation with three angular degrees of freedom. Determining a 5D position of a medical device may involve determining a location in a 3D coordinate system and an orientation with two angular degrees of freedom or a location in a 2D coordinate system and an orientation with three angular degrees of freedom.

Determining a 6D position of a medical device may involve determining a location in a 3D coordinate system and an orientation with three angular degrees of freedom.

In some embodiments, the positions determined at acts 356 and 358 are expressed in relationship with an RF interrogator system reference frame—e.g., a coordinate system associated with an interrogator system. In some embodiments, the location of the interrogator system defines the origin (or another reference point) of the RF interrogator reference system. One representative RF interrogator system reference frame is illustrated in FIG. 3B. As shown in this figure, the position of the patient support determined at act 356 (patient support position 310) is expressed in relationship with RF interrogator system reference frame 300, a coordinate system associated with interrogator system 101. Further, the position of the medical device determined at act 358 (medical device position 312) is also expressed in relationship with RF interrogator system reference frame 300.

At act 360, the controller determines a transformation between the RF interrogator system reference frame and a patient support reference frame, a coordinate system associated with the patient support. In some embodiments, the location of the patient support (e.g., the location of the target device(s) of the patient support or another location of the patient support, such as the center or a corner) defines the origin (or another reference point) of the patient support reference frame. For example, in some of the embodiments in which the patient support includes more than one target device, the location of one of the target devices of the patient support may define the origin of the patient support reference frame. Alternatively, the location of the geometric center of the target devices of the patient support may define the origin of the patient. Other locations relative to the target devices may be chosen to define the origin of the patient support reference frame. Referring again to FIG. 3B, transformation 301 represents a transformation between an RF interrogator system reference frame 302 and a patient support reference frame 302. Transformation 301 may be determined, for example, by determining a transformation matrix (e.g., a homogeneous transformation matrix) between the two reference frames using any suitable algorithm. In some embodiments, a transformation matrix between two reference frames may be determined using at least three positions within the first reference frame and at least three positions within the second reference frame. For example, in some embodiments the transformation 301 may be determined using the Kabsch algorithm. Additional aspects of the Kabsch algorithm are described in "A solution for the best rotation to relate two sets of vectors," Kabsch, W., Acta Cryst A 1976; 32:9223 and "A discussion of the solution for the best rotation to relate two sets of vectors," Kabsch, W., Acta Cryst A 1978; 34:8278, both of which are incorporated herein by reference in their entirety. It should be noted that act 360 may be performed in real time or may be pre-performed. In some embodiments, act 360 is performed during the course of a medical procedure, for example, every time the controller determines the current position of a medical device. In other embodiments, however, act 360 is performed one time, for example, before the beginning of a medical procedure.

At act 362, the controller determines, using the transformation determined at act 360, the position of the medical device in relationship with the patient support reference frame. For example, the controller may apply the transformation matrix determined at act 360 to the position of the medical device determined at act 358. Optionally, the controller further determines the position of the patient support in relationship with the patient support reference frame. This determination may be performed, for example, if the patient support is expected to move during the course of a medical procedure. Referring again to FIG. 3B, the position of the medical support determined at act 362 (medical support position 322) is expressed in relationship with patient support reference frame 302. Similarly, the position of the patient support determined at act 362 (patient support position 320) is expressed in relationship with the patient support reference frame 302.

In some embodiments, the position of the medical device may vary with respect to the position of the patient support during the course of a medical position. In these embodiments, process 350 may be repeated in an iterative fashion to track the relative position of the medical device with respect to the patient support in real time. Act 360 may be performed in real time or may be performed one time before the beginning of the medical procedure. Alternatively, act 360 may be performed in response to motion of the patient support relative to the previous position.

In some embodiments, the controller is configured to determine a target position (e.g., target location and/or target orientation) to which to move a medical device in order to perform the task with respect to patient 202. In one example, the medical device is an imaging device configured to image a patient, and the target position is a previous position of the imaging device (e.g., during a previous medical procedure or during a previous portion of the current medical procedure). This scenario may occur when it is desirable to re-image a previously imaged portion of the patient's body. Alternatively, the target position is a position that is offset, by a certain amount, from a previous position of the imaging device. This scenario may occur when it is desirable to stitch together multiple images taken at different times. Whether it is desirable to re-image a previously imaged portion of a patient or to stitch together multiple images taken at different times, determining the target position may first involve identifying a portion of the patient that was previously imaged. In another example, the medical device is a surgery tool, and the target position represents a particular portion of the patient's body in need of treatment. In yet another example, the medical device is a radiation device, and the target position represents a particular portion of the patient's body in need of radiation. In yet another example, the medical device is a medication delivery device, and the target position represents a particular portion of the patient's body in need of medication.

Figure 4:
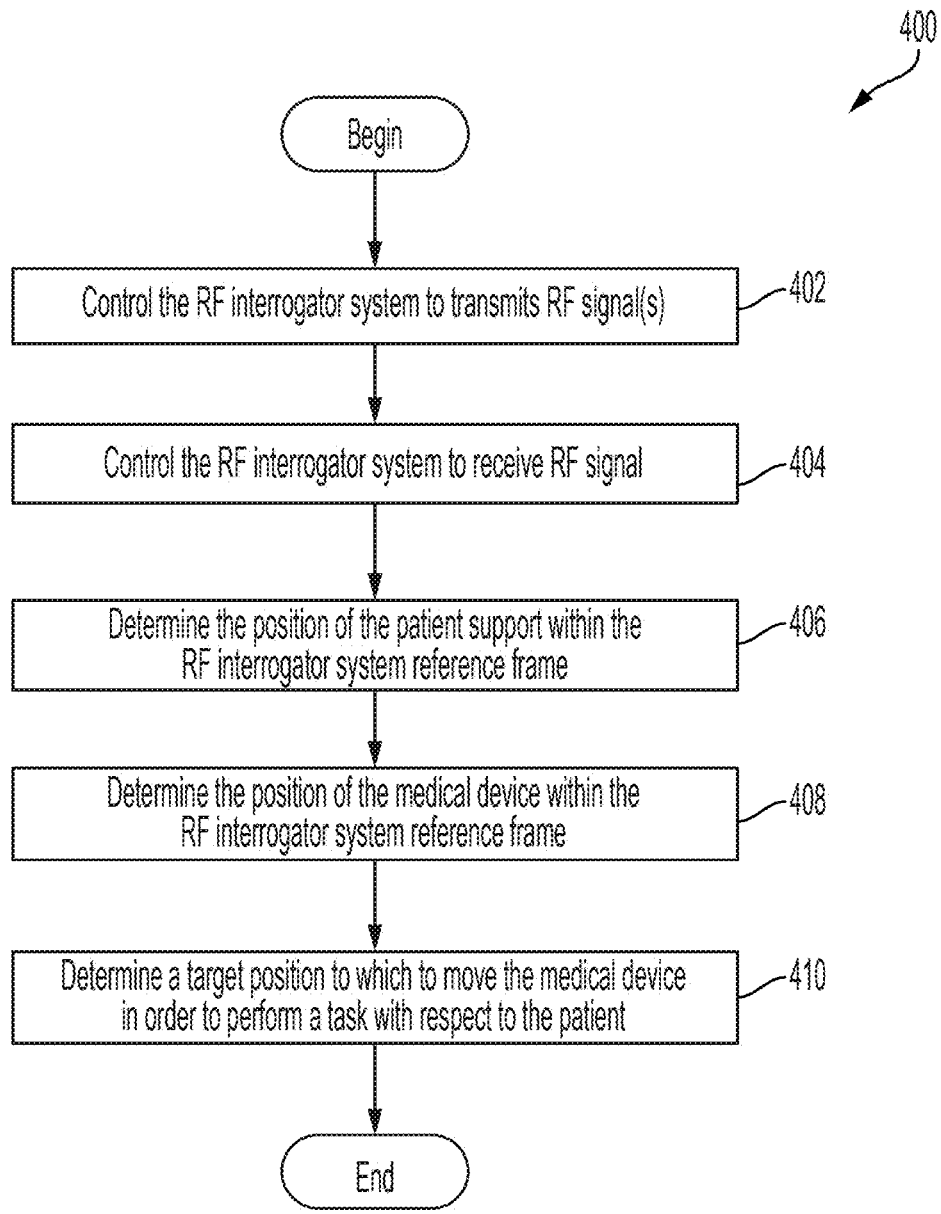
FIG. 4 is a flowchart illustrating a process for determining a target position to which to move a medical device, in accordance with some embodiments of the technology described herein.

FIG. 4 is a flowchart illustrating a process for determining a target position to which to move a medical device, in accordance with some embodiments of the technology described herein. Process 400 begins at act 402, which may mirror act 352 of process 350. Act 404 may mirror act 354 of process 350. Act 406 may mirror act 356 of process 350. Act 408 may mirror act 358 of process 350. At act 410, the controller determines a target position (e.g., location and/or orientation) to which to move the medical device in order to perform a task with respect to the patient. The task may involve for example imaging, deforming, treating, stitching, cutting or operating the patient or a portion of the patient's body. Determining the target position may involve determining a particular portion of the patient's body, such as the portion of the patient's body at which a previous medical procedure was interrupted. Alternatively, determining the target position may involve determining a location of the patient's body that was previously imaged. Alternatively, determining the target position may involve determining a portion of the patient's body in need of treatment or medication.

In some embodiments, the controller is further configured to determine a travel vector for the medical device within the patient support reference frame. The travel vector may be a vector between a current position of a medical device within the patient support reference frame and a target position of the medical device within the patient support reference frame. The controller may be configured to determine the travel vector using a current position of the medical device within the RF interrogator system reference frame, the target position within the RF interrogator system reference frame, and the transformation 301. For example, the controller may be configured to determine a difference between the current position and the target position of the medical device within the RF interrogator system reference frame, and thereafter, to apply the transformation 301 to determine the travel vector within the patient support reference frame. Alternatively, in some embodiments the controller may be configured to use the transformation 301 to determine the current and target positions within the patient support reference frame, and thereafter, to determine the travel vector within the patient support reference frame based on the difference between the current and target positions within the patient support reference frame.

In some embodiments, the controller is further configured to generate a command to cause the medical device to move to the target position. In one example, the controller may be configured to generate a command intended to cause a mechanism (e.g., a motor) to move the medical device. In another example, the controller may be configured to generate a command intended to facilitate manual motion of the medical device. For example, the controller may output instructions (e.g., audio, textual or visual instructions) intended to guide medical personnel to move the medical device to the target location.

In some embodiments, the controller is further configured to control the medical device to perform a task with respect to a patient. For example, the controller may control a robotic arm to assist medical personnel in performing a task with respect to a patient, or may control a robotic arm to perform a task with respect to the patient without human intervention or with limited human intervention. The controller may guide an end effector of the robotic arm to grasp a surgical tool and to use the surgical tool on the patient, or to use the end effector directly on the patient. In another example, the controller may control an imaging device to scan a portion of the patient's body. In yet another example, the controller may control a medication delivery device to administer medication at a desired location of the patient's body. In yet another example, the controller may control a radiation device to administer radiation at a desired location of the patient's body.

Figure 5B:
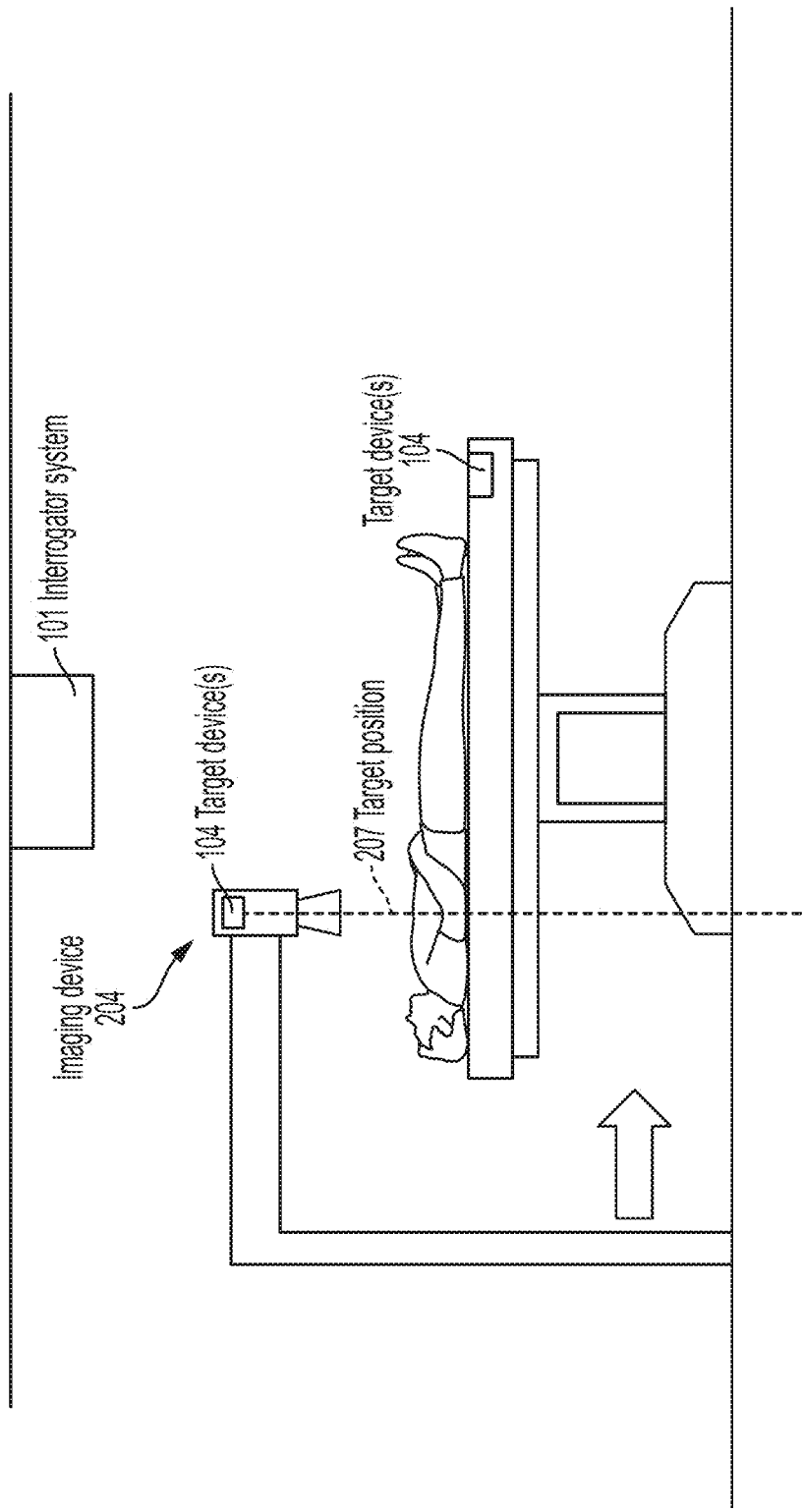
FIG. 5B shows the RF co-localization system of FIG. 5A with the imaging device positioned at a target position, in accordance with some embodiments of the technology described herein.

FIGS. 5A-5B depict an environment including an imaging device 204, in accordance with some embodiments. In the illustrative step depicted in FIG. 5A, controller 106 determines a target position 207 to which to move imaging device 204 to image patient 202. Determining target position 207 may be performed using process 400. Target position 207 may be, for example, a position at which imaging device 204 had previously imaged patient 202 (e.g., during a previous medical procedure or during a previous portion of the current medical procedure). Thus, determining the target position may allow the imaging device to re-image a previously imaged portion of the patient's body. Alternatively, the target position is a position that is offset from a position at which the imaging device had previously imaged the patient. Thus, determining the target position may allow the imaging device to stitch together images taken at different times. In the illustrative step depicted in FIG. 5B, controller 106 controls imaging device 204 to move to target position 207. Subsequently, controller 106 may control imaging device 204 to image the patient at target position 207.

Figure 6A:
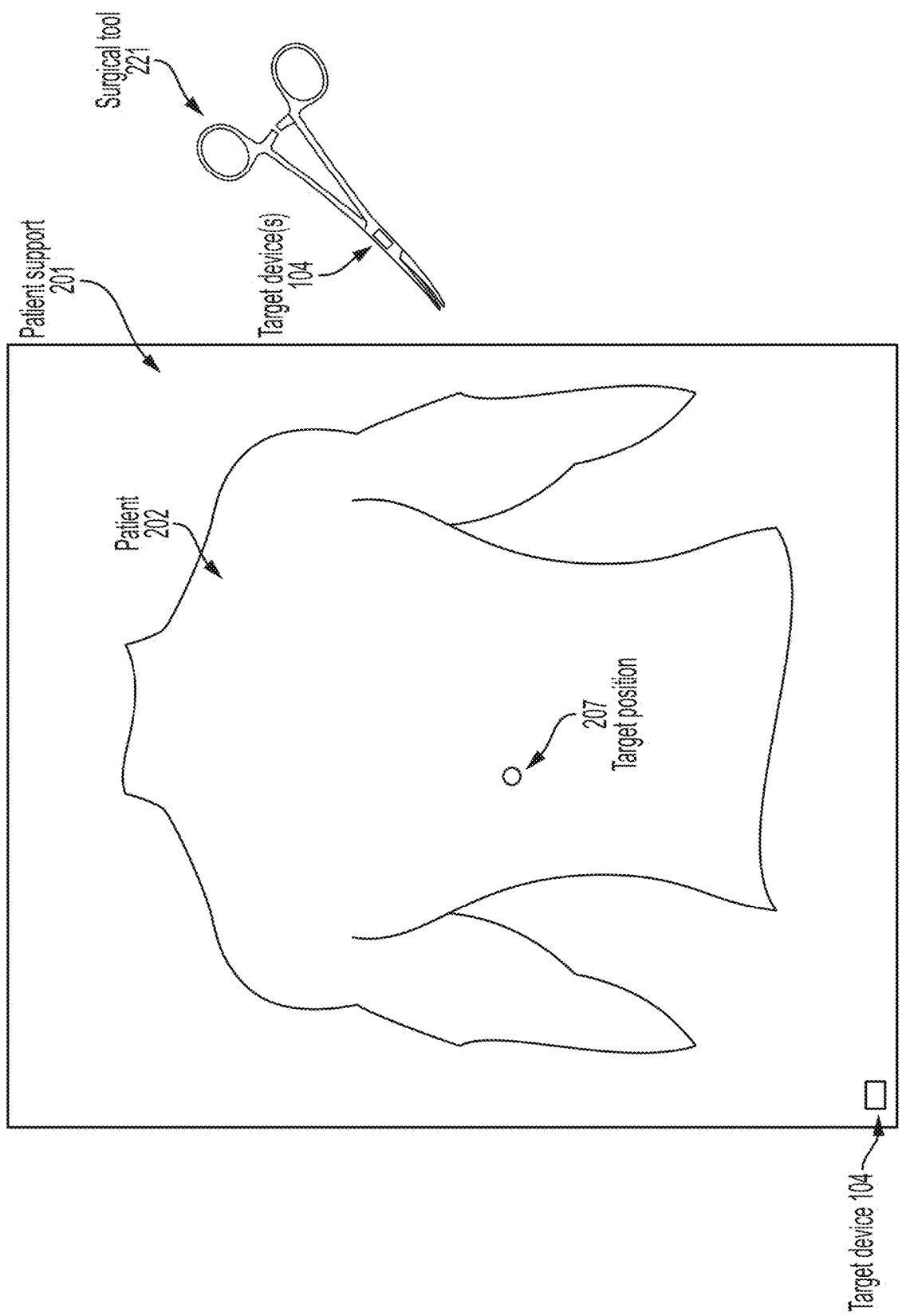
FIG. 6A shows an RF co-localization system configured to use RF localization techniques to facilitate interactions between a surgical tool and a patient, in accordance with some embodiments of the technology described herein.
Figure 6B:
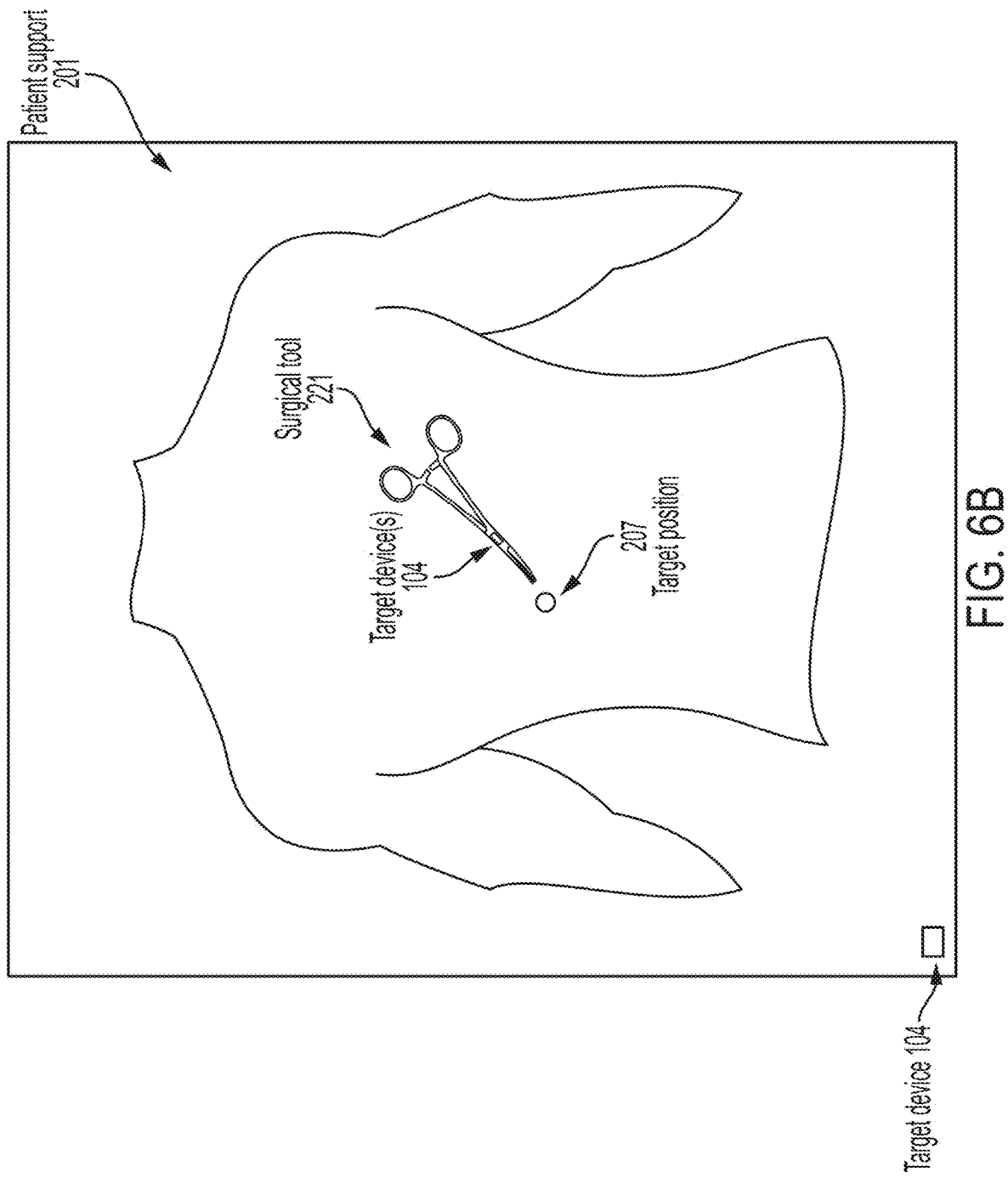
FIG. 6B shows the RF co-localization system of FIG. 6A with the surgical tool positioned at a target position, in accordance with some embodiments of the technology described herein.

FIGS. 6A-6B depict an environment including a surgical tool 221, in accordance with some embodiments. Surgical tool 221 may be arranged to be handled by a human or by a robotic arm 210. In the illustrative step depicted in FIG. 6A, controller 106 determines a target position 207 to which to move surgical tool 221 or to assist (using audio, text or visual aid) a human to move surgical tool 221. Determining target position 207 may be performed using process 400. Target position 207 may be, for example, a position at which patient 202 needs treatment or medication. Alternatively, target position 207 may be a position at which surgical tool 221 or a different tool had previously been used with respect to the patient (e.g., during a previous medical procedure or during a previous portion of the current medical procedure). Thus, determining the target position may allow medical personnel or a robotic arm to continue a procedure that was previously interrupted. Further, determining the target position may help medical personnel identify organs that are not easy to reach.

In the illustrative step depicted in FIG. 6B, controller 106 may control a robotic arm to move surgical tool 221 to target position 207 or may assist a human to move surgical tool 221 to target position 207. Subsequently, controller 106 may control the robotic arm to treat patient 202 using surgical tool 221 at target position 207 or may assist a human to treat the patient using surgical tool 221 at target position 207.

In some embodiments, controller 106 may overlay real time images (e.g., X-rays images or ultrasound images, among other example) of patient 202 with information relating to the position of a surgical tool. Such an image may be displayed in real time on a screen that is either placed in the environment or at a remote location. This provides a surgeon with information indicative of the position of a surgical tool relative to a particular organ in a real time fashion. In some embodiments, controller 106 may control the position of an image device relative to the position of a patient support and, at the same time, may track the position of a surgical tool. The controller may further control a display to display a sequence of images taken by the imaging device in real time, and to provide a visual indication of the position of the surgical tool relative to the images.

In some embodiments, controller 106 may uniquely identify objects in an environment using RF signals. In this way, controller 106 may distinguish a medical device from another medical device, such as a surgical tool from another surgical tool, an imaging device from another imaging device, a medication from another medication, a medication from an imaging device, an imaging device from a surgical tool, etc. Additionally, controller 106 may identify one particular medical device from among a set of like medical devices.

In some embodiments, a controller may uniquely identify a target device based on a predefined transmission schedule (referred to as "time-domain identification"). For example, the controller may assign a time slot to each target device, and may determine which target device has responded to an interrogation signal on the basis of the time of arrival of the response signal. Consider a representative scenario in which a particular target device is assigned the first time slot. The controller can determine the identity of the target device from the fact that the interrogator system received a response signal during the first time slot.

In some embodiments, an interrogator system may transmit an RF signal—referred to as the scheduling signal—informing the target devices which target device is assigned to which time slot. This RF signal may be transmitted at a center frequency different from the center frequency of the interrogation signal. For example, the interrogation signal may have a center frequency of 60 GHz, and the scheduling signal may have a center frequency of 900 MHz, for example.

In other embodiments, identification of medical devices may involve encoding RF signals with information uniquely associated to particular medical devices (referred to as "code-domain identification"). For example, in response to receiving an RF signal from an interrogator device, a target device may transmit another RF signal that is encoded with a number uniquely identifying that target device. Alternatively, in response to receiving an RF signal from an interrogator device, a target device may transmit another RF signal that is encoded with a number uniquely identifying a set of target device associated with a particular medical device. In these embodiments, instead of having a unique code for each target devices, the target devices affixed to a common medical device may share the same code.

In yet other embodiments, identification of medical devices may involve different response frequencies, where each response frequency is uniquely associated to a particular medical device (referred to as "frequency-domain identification"). For example, in response to receiving an interrogating signal, one target device transmits RF signals at a first center frequency and another target device transmits RF signals at a second center frequency. The controller can uniquely identify target devices on the basis of the received center frequency.

The RF localization techniques described herein may be used in some embodiments with other localization techniques. For example, the RF localization techniques described herein may be used to enhance other localization techniques in medical settings. One such localization technique is retroreflective marker tracking. Retroreflective marker tracking systems rely on objects having one or more markers affixed thereto. These markers may be active markers (e.g., light emitting diode markers), passive markers (e.g., retroreflective markers), or a combination of active and passive markers. In a medical setting, a physician may treat the surface of a patient's body using the distal tip of a surgical tool. A marker sensing device (e.g., a pair of cameras) views the markers affixed to the surgical tool. On the basis of the known locations of the cameras and the location of the markers as seen by each camera, such systems calculate the three-dimensional coordinates of the markers. Then, on the basis of the known relationship between the location of the markers and the location of the tip of the surgical tool, the marker-tracking system determines the coordinates of the tip.

Figure 7A:
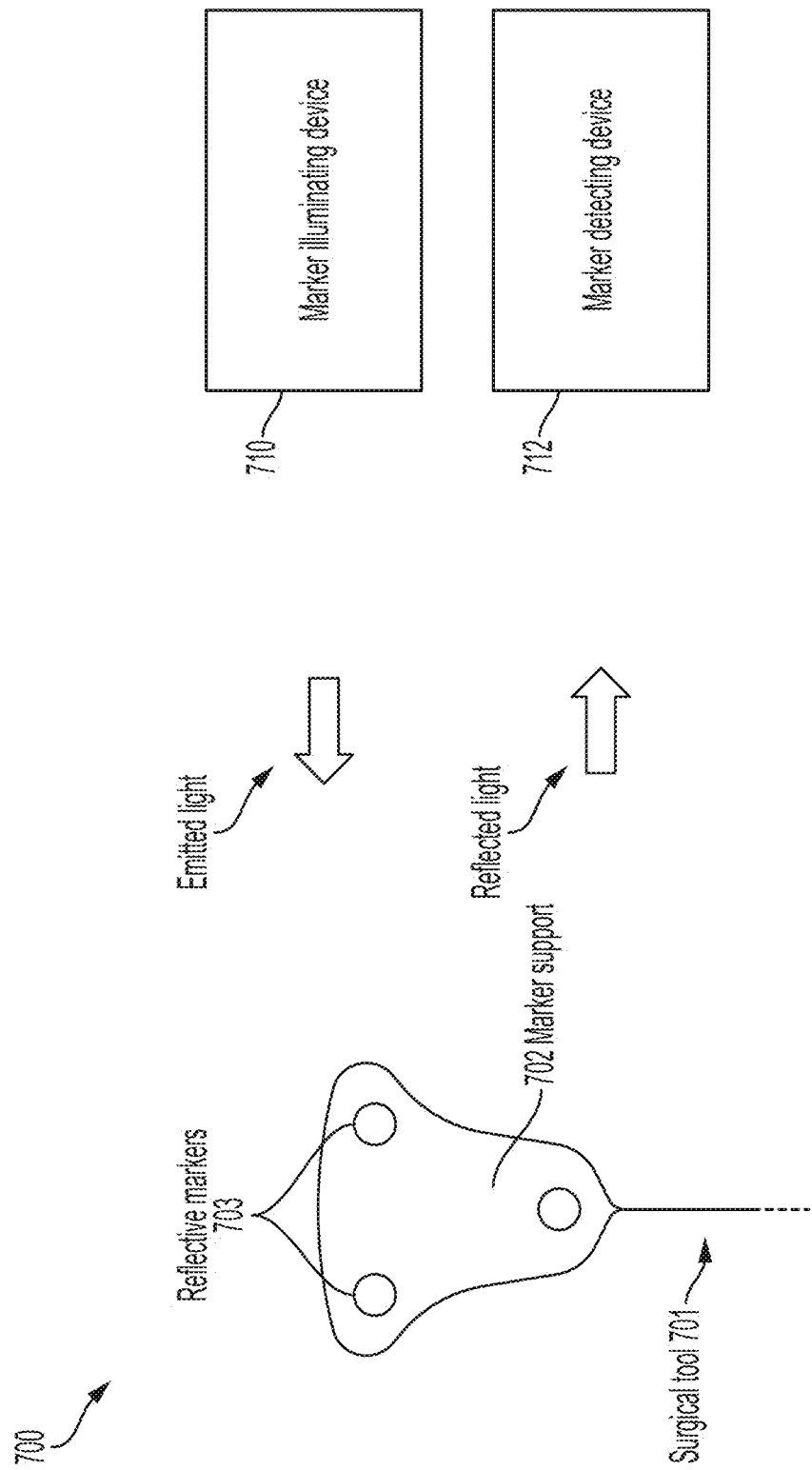
FIG. 7A is a schematic diagram illustrating a retroreflective marker tracking system.

FIG. 7A illustrates a representative retroreflective marker tracking system. System 700 includes a marker support 702 attached to a surgical tool 701, a marker illuminating device 710 (e.g., a light source) and a marker detecting device 712 (e.g., a photosensitive device such as a camera). Reflective markers 703 are affixed to marker support 702. Reflective markers 703 may be shaped as spheres, for example, and may be made of or otherwise coated with a reflective material.

System 700 is configured to localize surgical tool 701. Marker illuminating device 710 is configured to emit light towards the surgical tool to be localized. The emitted light is reflected by the markers, and the reflected light is captured by marker detecting device 712. Marker detecting device 712 generates data indicative of the location of the detected retroreflective markers in space, and provides the data to a computing device. Given the known locations of marker detecting device 712 and the locations of the markers 703, the computing device calculates the location and/or orientation of surgical tool 701. Further, on the basis of the known relationship between the location/orientation of each of the markers and the location of a tip of the surgical tool, the computing device calculates the coordinates of the tip of the surgical tool in space.

In system 700, object identification is performed on the basis of the spatial arrangement of the reflective markers affixed to a particular object. Each object has markers that are arranged in a unique arrangement. For example, one surgical tool may have four markers that are all aligned to each other, and another surgical tool may have four markers arranged to form a square. Marker detection device 712 can uniquely identify these surgical tools from one another on the basis of the pattern of the reflected light, which depends on the specific arrangement of the reflective markers causing the light reflection. Object identification in an environment including several objects may be performed based on this technique by defining an alphabet of marker arrangements.

The inventors have appreciated that RF localization techniques may be used to enhance the localization accuracy of retroreflective marker tracking systems. For example, the RF localization techniques described herein may allow retroreflective marker tracking systems to operate at sub-millimeter resolutions. FIG. 7B illustrates a surgical tool 701 having one or more target devices 104 in addition to reflective markers 703. In this example, the target device(s) 104 and reflective markers 703 are affixed to marker support 702, though other arrangements are also possible. For example, reflective markers 703 may be affixed to marker support 702 and target device(s) 104 may be affixed directly to surgical tool 701.

Figure 7C:
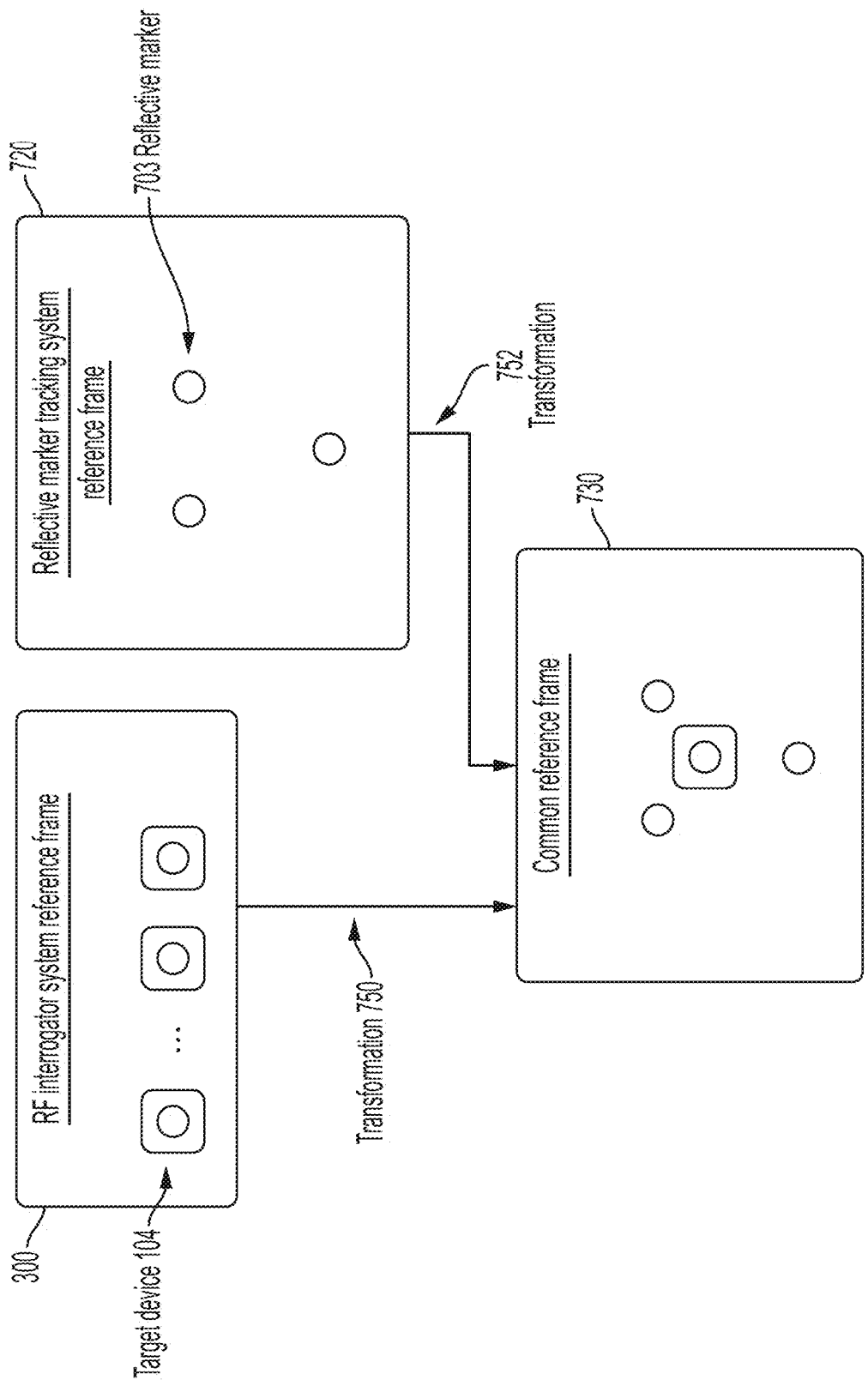
FIG. 7C is a block diagram illustrating a hybrid localization system, in accordance with some embodiments of the technology described herein.

In the depiction of FIG. 7B, an RF localization system operates in conjunction with a retroreflective marker tracking system to localize a medical device. Patient supports may also be localized using these two localization systems. The manner in which these systems interact with each other is depicted in FIG. 7C, in accordance with some embodiments. The RF localization system determines the positions of the target devices 104 of a particular medical device within the RF interrogator system reference frame 300. The origin of RF interrogator system reference frame 300 may be defined, for example, at the location of interrogator system 101. Additionally, the retroreflective marker tracking system determines the positions of the reflective markers 703 of the same medical device within the reflective marker tracking system reference frame 720. The origin of reflective marker tracking system reference frame 720 may be defined, for example, at the location of marker detecting device 712.

In some embodiments, one or more transformation(s) may be used to determine the positions of the target devices and the reflective markers with respect to a common reference frame 730. Any reference frame may be chosen to serve as the common reference frame. In one example, RF interrogator system reference frame 300 may be chosen as the common reference frame. In another example, reflective marker tracking system reference frame 720 may be chosen as the common reference frame. In yet another example, a patient support reference frame (e.g., patient support reference frame 302 of FIG. 3B) may be chosen as the common reference frame. Transformation 750 transforms coordinates from RF interrogator system reference frame 300 to common reference frame 730. In embodiments in which RF interrogator system reference frame 300 itself is chosen as the common reference frame 730, transformation 750 may include an identity matrix. In embodiments in which a patient support reference frame is chosen as the common reference frame 730, transformation 750 equals transformation 301 of FIG. 3B. Similarly, transformation 752 transforms coordinates from reflective marker tracking system reference frame 720 to common reference frame 730. In embodiments in which reflective marker tracking system reference frame 720 itself is chosen as the common reference frame 730, transformation 750 may include an identity matrix. It should be noted that the scheme of FIG. 7C applies not only to RF localization systems operating in conjunction with marker tracking system reference frame 720, but also to RF localization systems operating in conjunction with other types of companion localization systems. The companion localization system may define its own companion system reference frame.

Having thus described several aspects of at least one embodiment of this technology, it is to be appreciated that various alterations, modifications, and improvements will readily occur to those skilled in the art.

The above-described embodiments of the technology described herein can be implemented in any of numerous ways. For example, the embodiments may be implemented using hardware, software, or a combination thereof. When implemented in software, the software code can be executed on any suitable processor or collection of processors, whether provided in a single computer or distributed among multiple computers. Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semi-custom circuitry resulting from configuring a programmable logic device. As yet a further alternative, a processor may be a portion of a larger circuit or semiconductor device, whether commercially available, semi-custom or custom. As a specific example, some commercially available microprocessors have multiple cores such that one or a subset of those cores may constitute a processor. Though, a processor may be implemented using circuitry in any suitable format.

Also, the various methods or processes outlined herein may be coded as software that is executable on one or more processors running any one of a variety of operating systems or platforms. Such software may be written using any of a number of suitable programming languages and/or programming tools, including scripting languages and/or scripting tools. In some instances, such software may be compiled as executable machine language code or intermediate code that is executed on a framework or virtual machine. Additionally, or alternatively, such software may be interpreted.

The techniques disclosed herein may be embodied as a non-transitory computer-readable medium (or multiple computer-readable media) (e.g., a computer memory, one or more floppy discs, compact discs, optical discs, magnetic tapes, flash memories, circuit configurations in Field Programmable Gate Arrays or other semiconductor devices, or other non-transitory, tangible computer storage medium) encoded with one or more programs that, when executed on one or more processors, perform methods that implement the various embodiments of the present disclosure described above. The computer-readable medium or media may be transportable, such that the program or programs stored thereon may be loaded onto one or more different computers or other processors to implement various aspects of the present disclosure as described above.

The terms "program" or "software" are used herein to refer to any type of computer code or set of computer-executable instructions that may be employed to program one or more processors to implement various aspects of the present disclosure as described above. Moreover, it should be appreciated that according to one aspect of this embodiment, one or more computer programs that, when executed, perform methods of the present disclosure need not reside on a single computer or processor, but may be distributed in a modular fashion amongst a number of different computers or processors to implement various aspects of the present disclosure.

Various aspects of the technology described herein may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the technology described herein may be embodied as a method, examples of which are provided herein including with reference to FIGS. 1D, 3A and 4. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The terms "approximately" and "about" may be used to mean within ±20% of a target value in some embodiments, within ±10% of a target value in some embodiments, within ±5% of a target value in some embodiments, within ±2% of a target value in some embodiments, within ±1% in some embodiments. The terms "approximately" and "about" may include the target value.

What is claimed is:

1. A system, comprising:
    a radio-frequency (RF) interrogator system;
    one or more first RF target devices for coupling to a patient support for supporting a patient with respect to whom a medical device is to perform a task;
    one or more second RF target devices for coupling to the medical device; and
    a controller configured to, when the one or more first RF target devices are coupled to the patient support and the one or more second RF target devices are coupled to the medical device:
        control the RF interrogator system to transmit one or more first RF signals;
        control the RF interrogator system to receive:
            one or more second RF signals transmitted by the one or more first RF target devices responsive to the one or more first RF signals; and
            one or more third RF signals transmitted by the one or more second RF target devices responsive to the one or more first RF signals;
        determine, using the received one or more second RF signals, a position of the patient support within an RF interrogator system reference frame;
        determine, using the received one or more third RF signals, a first position of the medical device within the RF interrogator system reference frame;
        determine a transformation between the RF interrogator system reference frame and a patient support reference frame; and
        determine, using the transformation, a second position of the medical device within the patient support reference frame.

2. The system of claim 1, wherein the controller is further configured to control the medical device, using the second position of the medical device within the patient support reference frame, to perform the task with respect to the patient.

3. The system of claim 1, wherein the one or more first RF target devices comprise a first RF target device and a second RF target device, and wherein determining a position of the patient support comprises determining a vector between the RF interrogator system and the first RF target device and a vector between the RF interrogator system and the second RF target device.

4. The system of claim 1, wherein the medical device is a first medical device, and wherein the system further comprises one or more third RF target devices for coupling to a second medical device, wherein the controller is further configured to distinguish the first medical device from the second medical device using the received one or more third RF signals.

5. The system of claim 1, wherein the medical device comprises at least one selected from the group consisting of a grasper, forceps, a clamp, an occlude, a drill, a plier, a needle driver, a needle holder, a retractor, a distractor, a positioner, a stereotactic device, a mechanical cutter, a dilators a speculum, a suction tip, a tube, an irrigation needle, an injection needle, a dermatomes, a scope, a probe, a carrier, an applier, a cryotome, a cutting laser guide, a measurement device.

6. The system of claim 1, wherein the one of more first RF signals have a center frequency of 50-70 GHz.

7. The system of claim 1, wherein the controller is configured to determine the transformation by determining a matrix using at least three positions within the RF interrogator system reference frame and at least three positions within the patient support reference frame.

8. The system of claim 1, wherein the controller is configured to determine the transformation prior to controlling the RF interrogator system to transmit one or more first RF signals.

9. A method performed by a controller part of a system, the system comprising: (i) the controller, (ii) a radio-frequency (RF) interrogator system, (iii) one or more first RF target devices for coupling to a patient support for supporting a patient with respect to whom a medical device is to perform a task, and (iv) one or more second RF target devices for coupling to the medical device, the method comprising:
    when the one or more first RF target devices are coupled to the patient support and the one or more second RF target devices are coupled to the medical device, using the controller to perform:
        controlling the RF interrogator system to transmit one or more first RF signals;
        controlling the RF interrogator system to receive:
            one or more second RF signals transmitted by the one or more first RF target devices responsive to the one or more first RF signals; and
            one or more third RF signals transmitted by the one or more second RF target devices responsive to the one or more first RF signals;
        determining, using the received one or more second RF signals, a position of the patient support within an RF interrogator system reference frame;
        determining, using the received one or more third RF signals, a first position of the medical device within the RF interrogator system reference frame;
        determining a transformation between the RF interrogator system reference frame and a patient support reference frame; and determining, using the transformation, a second position of the medical device within the patient support reference frame.

10. The method of claim 9, further comprising controlling the medical device, using the second position of the medical device within the patient support reference frame, to perform the task with respect to the patient.

11. The method of claim 10, wherein the medical device comprises an imaging device, and wherein controlling the medical device to perform the task with respect to the patient comprises controlling the imaging device to image the patient.

12. The method of claim 10, wherein the medical device comprises a surgical tool, and wherein controlling the medical device to perform the task with respect to the patient comprises controlling the surgical tool to treat the patient.

13. The method of claim 9, wherein the medical device is a first medical device, and wherein the system further comprises one or more third RF target devices for coupling to a second medical device, wherein the method further comprises distinguishing the first medical device from the second medical device using the received one or more third RF signals.

14. The method of claim 9, wherein determining the transformation comprises determining a matrix using at least three positions within the RF interrogator system reference frame and at least three positions within the patient support reference frame.

15. A system, comprising:
a radio-frequency (RF) interrogator system;
one or more first RF target devices for coupling to a patient support for supporting a patient with respect to whom a medical device is to perform a task;
one or more second RF target devices for coupling to the medical device; and
a controller configured to, when the one or more first RF target devices are coupled to the patient support and the one or more second RF target devices are coupled to the medical device:
control the RF interrogator system to transmit one or more first RF signals;
control the RF interrogator system to receive:
one or more second RF signals transmitted by the one or more first RF target devices responsive to the one or more first RF signals; and
one or more third RF signals transmitted by the one or more second RF target devices responsive to the one or more first RF signals;
determine, using the received one or more second RF signals, a first position of the patient support within an RF interrogator system reference frame;
determine, using the received one or more third RF signals, a second position of the medical device within the RF interrogator system reference frame; and
determine, using the first and second positions, a target position to which to move the medical device in order to perform the task with respect to the patient.

16. The system of claim 15, wherein the controller is further configured to generate a command to cause the medical device to move to the target position in order to perform the task with respect to the patient.

17. The system of claim 15, wherein the controller is further configured to:
determine, using information received from a companion localization system, a third position of the medical device within a companion system reference frame; and
determine the target position further using the third position.

18. The system of claim 17, wherein the companion system comprises:
a plurality of reflective markers connected to the medical device and configured to reflect light, wherein the controller is configured to determine the third position using positions of the plurality of markers in the companion system reference frame.

19. The system of claim 15, wherein determining the target position comprises identifying a portion of the patient in need of treatment.

20. The system of claim 15, wherein determining the target position comprises identifying a portion of the patient previously imaged.

* * * * *